(12) United States Patent
Stiene

(10) Patent No.: US 7,901,875 B2
(45) Date of Patent: *Mar. 8, 2011

(54) ANALYTE TEST SYSTEM FOR DETERMINING THE CONCENTRATION OF AN ANALYTE IN A PHYSIOLOGICAL OR AQUEOUS FLUID

(75) Inventor: Matthias Stiene, Gilching (DE)

(73) Assignee: Egomedical Swiss AG, Oberuzwil (CH)

( * ) Notice: Subject to any disclaimer, the term of this patent is extended or adjusted under 35 U.S.C. 154(b) by 1457 days.

This patent is subject to a terminal disclaimer.

(21) Appl. No.: 11/073,254

(22) Filed: Mar. 4, 2005

(65) Prior Publication Data

US 2005/0196747 A1 Sep. 8, 2005

Related U.S. Application Data

(63) Continuation-in-part of application No. PCT/EP2004/002284, filed on Mar. 5, 2004.

(30) Foreign Application Priority Data

Feb. 16, 2005 (EP) .................................. 05003296

(51) Int. Cl.
  *C12Q 1/00* (2006.01)
  *G01N 15/06* (2006.01)
  *G01N 25/08* (2006.01)
(52) U.S. Cl. ............. 435/4; 422/68.1; 422/73; 427/2.12; 427/209; 436/150; 600/309
(58) Field of Classification Search .................. None
See application file for complete search history.

(56) References Cited

U.S. PATENT DOCUMENTS

| | | | |
|---|---|---|---|
| 4,687,529 A | * | 8/1987 | Wang .............................. 156/163 |
| 4,761,381 A | | 8/1988 | Blatt et al. |
| 4,849,340 A | | 7/1989 | Oberhardt et al. |
| 5,144,139 A | | 9/1992 | Hillman et al. |
| 5,628,890 A | | 5/1997 | Carter et al. |
| 5,628,961 A | | 5/1997 | Davis et al. |
| 5,629,209 A | | 5/1997 | Braun et al. |

(Continued)

FOREIGN PATENT DOCUMENTS

DE 224 119 A1 6/1985

(Continued)

OTHER PUBLICATIONS

Koscielniak, P, Nonlinear calibration by the standard addition method, Chemometrics and Intelligent Laboratory Systems, 47 (1999), pp. 275-287.

(Continued)

*Primary Examiner* — Krishnan S Menon
*Assistant Examiner* — Dirk Bass
(74) *Attorney, Agent, or Firm* — Klauber & Jackson LLC

(57) ABSTRACT

This invention provides a device for determining the concentration of an analyte like glucose, cholesterol, free fatty acids, triglycerides, proteins, ketones, phenylalanine or enzymes, in a physiological or aqueous fluid like blood, serum, plasma, saliva, urine, interstitial and/or intra-cellular fluid, the device having an integrated calibration and quality control system suitable for dry reagent test strips with a very small sample volume of about 0.5 μL based on to a new sample distribution system. The production of the inventive analyte test element involves only a small number of uncomplicated production steps enabling an inexpensive production of the strips.

25 Claims, 22 Drawing Sheets

U.S. PATENT DOCUMENTS

| | | | |
|---|---|---|---|
| 5,711,861 A | 1/1998 | Ward et al. | |
| 6,165,739 A | 12/2000 | Clatch et al. | |
| 6,251,083 B1 | 6/2001 | Yum et al. | |
| 6,922,578 B2 * | 7/2005 | Eppstein et al. | 600/347 |
| 2002/0130042 A1 | 9/2002 | Moerman et al. | |
| 2002/0168290 A1 * | 11/2002 | Yuzhakov et al. | 422/56 |
| 2003/0083385 A1 | 5/2003 | Gerlach et al. | |
| 2003/0083685 A1 | 5/2003 | Freeman et al. | |
| 2003/0210287 A1 | 11/2003 | Harding et al. | |
| 2004/0007585 A1 | 1/2004 | Griffith et al. | |
| 2004/0028566 A1 | 2/2004 | Ko et al. | |
| 2004/0031688 A1 | 2/2004 | Shenderov | |
| 2004/0241451 A1 | 12/2004 | Clark et al. | |
| 2005/0106713 A1 | 5/2005 | Phan et al. | |
| 2005/0196820 A1 | 9/2005 | Zweig | |
| 2007/0287191 A1 | 12/2007 | Stiene et al. | |
| 2009/0221011 A1 | 9/2009 | Stiene et al. | |
| 2010/0035245 A1 | 2/2010 | Stiene et al. | |
| 2010/0140116 A1 | 6/2010 | Stiene et al. | |

FOREIGN PATENT DOCUMENTS

| | | |
|---|---|---|
| DE | 3632379 | 3/1988 |
| DE | 19850501 | 5/2000 |
| EP | 0 018 435 B1 | 3/1984 |
| EP | 0400460 | 12/1990 |
| EP | 0 215 419 B1 | 5/1991 |
| EP | 0454967 | 11/1991 |
| EP | 0 503 914 | 9/1992 |
| EP | 0779226 | 8/1997 |
| EP | 0951939 | 10/1999 |
| EP | 0 757 921 B1 | 11/2002 |
| EP | 1 318 397 | 6/2003 |
| EP | 1 574 858 | 9/2005 |
| JP | 2000-042402 | 2/2000 |
| WO | 89/04474 | 5/1989 |
| WO | 93/22453 | 11/1993 |
| WO | 96/39343 | 12/1996 |
| WO | 00/56808 | 9/2000 |
| WO | 01/46038 | 6/2001 |
| WO | 02/76878 | 10/2002 |
| WO | WO 02/85185 | 10/2002 |
| WO | 03/083469 | 10/2003 |
| WO | 2005/072216 | 8/2005 |
| WO | 2006/015615 | 2/2006 |
| WO | 2006/015615 A1 | 2/2006 |

OTHER PUBLICATIONS

Heiss, et al., Analytica Chimica Acta, vol. 396(2/3), pp. 309-316 (1999).

Dosch, et al., Fresenius Journal of Analytical Chemistry, vol. 361(2), pp. 174-178, 1998.

English Translation of DD 224119.

International Search Report issued on Jan. 31, 2005 in International Application No. PCT/EP2004/009113.

Bass, D., Restriction Requirement issued on Jul. 31, 2009 in U.S. Appl. No. 11/073,254.

Bass, D., Non-Final Office Action issued on Dec. 2, 2009 in U.S. Appl. No. 11/073,254, pp. 1-9.

Haidekker, et al., Hydrophillic Molecular Rotor Derivatives - Synthesis and Characterization Bioorganic Chemistry, Online, vol. 4(32) pp. 274-289 (2004).

International Search Report and Written Opinioin issued on Mar. 10, 2006 in International Application No. PCT/EP2005/009382.

International Search Report and Written Opinion issued on Feb. 24, 2006 in International Application No. PCT/EP2005/009381.

International Seaerch Report and Written Opinoin issued on Apr. 4, 2008 in International Application No. PCT/EP2008/000679.

European Examination Report issued on Jun. 16, 2010 in European Application No. 05 782 632.3 - 2404.

Bass, D., Restriction Requirement issued on Jun. 12, 2009 in U.S. Appl. No. 11/659,968.

Bass, D., Non-Final Office Action issued on Sep. 30, 2009 in U.S. Appl. No. 11/659,968, pp. 1-9.

* cited by examiner

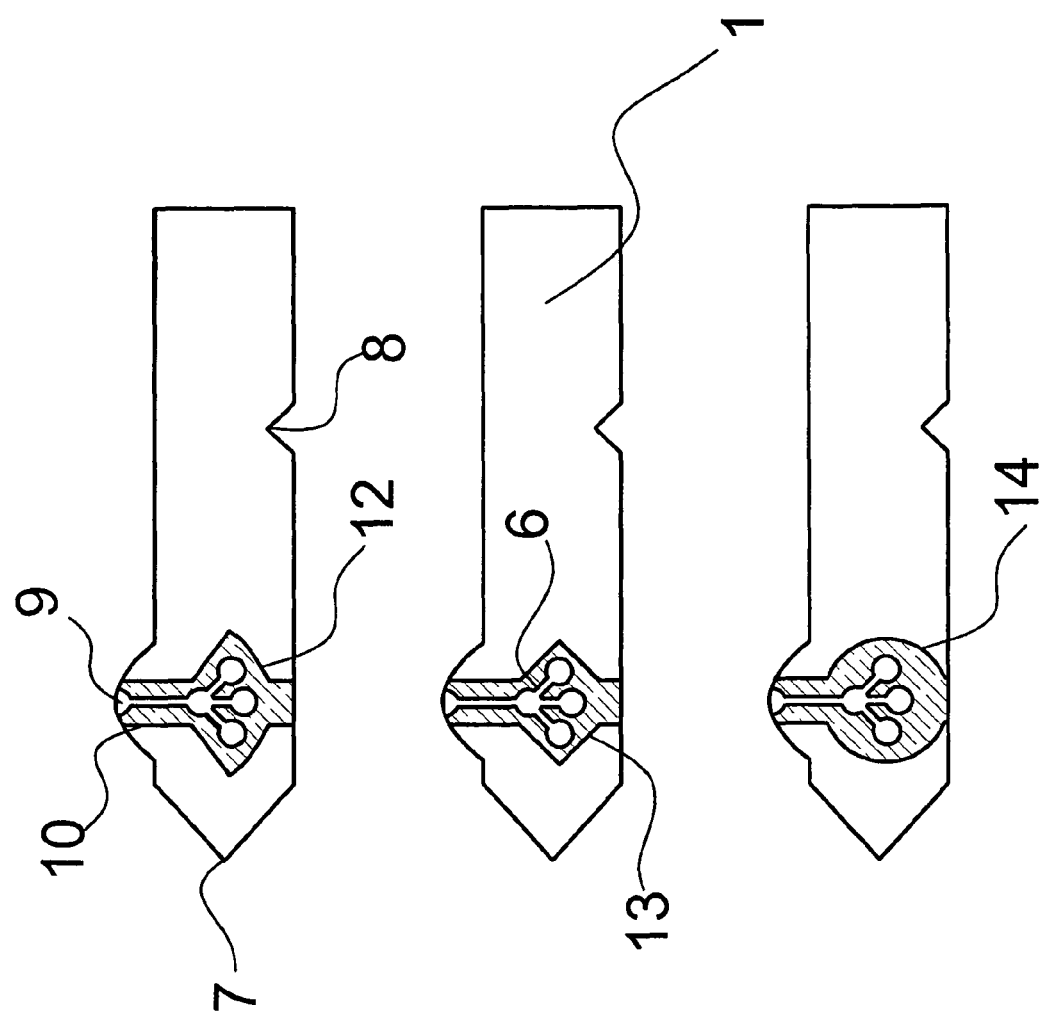

| | A | B | C | $n$ |
|---|---|---|---|---|
| I | | | 1st Order (linear) | 3 |
| II | | | 2nd Order (quadratic) | 4 |
| III | | | 3rd Order (cubic) | 5 |
| IV | | | 4th Order | 6 |

Fig. 7

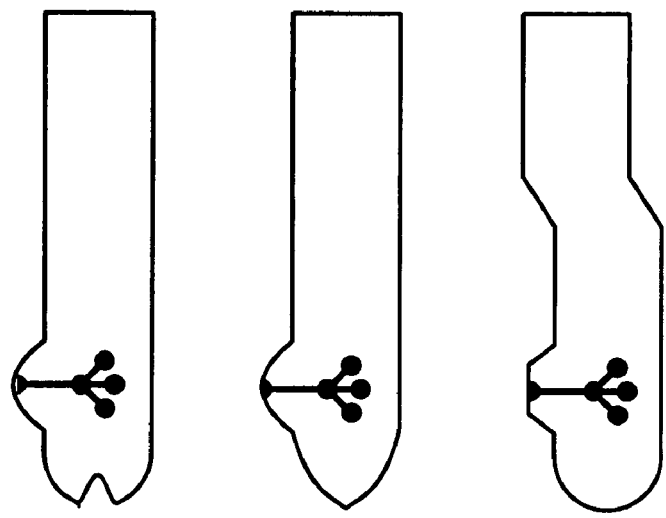
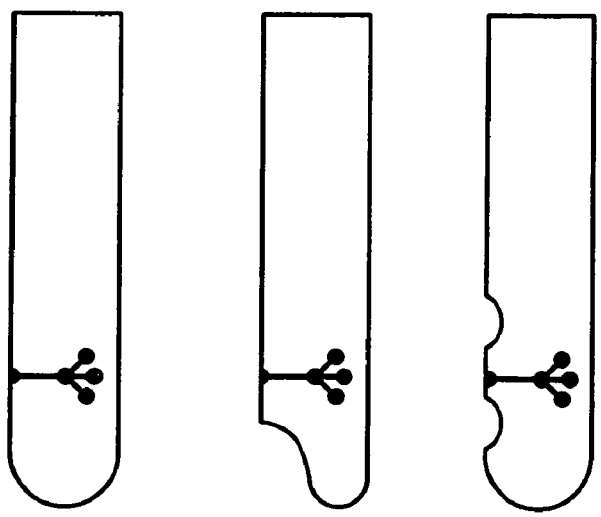
Fig. 11

ANALYTE TEST SYSTEM FOR DETERMINING THE CONCENTRATION OF AN ANALYTE IN A PHYSIOLOGICAL OR AQUEOUS FLUID

RELATED APPLICATIONS

The present application is a Continuation-In-Part of co-pending PCT Application No. PCT/EP2004/002284, filed Mar. 5, 2004 and also claims priority from European Patent Application Serial No. EP 05003296.0, filed Feb. 16, 2005. Applicants claim the benefits of 35 U.S.C. §120 as to the PCT application and priority under 35 U.S.C. §119 as to said European application, and the entire disclosures of both applications are incorporated herein by reference in their entireties.

FIELD OF THE INVENTION

This invention relates to the field of quantitative analysis of an analyte, e. g. glucose, in a physiological fluid, e. g. blood. More particularly, this invention provides an analyte test system and test method for the quantitative determination of analytes in a physiological or aqueous fluid and a method of preparation.

BACKGROUND OF THE INVENTION

The determination of analyte concentrations in physiological samples plays a prominent role in diagnosis and therapy of a variety of diseases. Analytes of interest include among others glucose, cholesterol, free fatty acids, triglycerides, proteins, ketones, phenylalanine, enzymes, antibodies, or peptides in blood, plasma, urine or saliva.

Typically, a physiological sample fluid, e. g. capillary blood, is applied to a test strip to evaluate the concentration of an analyte. The test strips are usually used in conjunction with a measuring device which measures some electrical properties, such as electrical current, if the strip is designed for detection of an electro-active compound, or for the measurement of light reflectance and/or transmittance, if the strip is designed for photometric detection. In systems with optical detection technology a mixture of enzymes and colour-generating materials known as chromogens is located on the test strip. The analyte contained in the physiological or aqueous fluid, which has been applied to the test strip, reacts with the reagents and causes a change in reflectance or transmittance thereby indicating the concentration of the analyte in the test sample.

For example, glucose is determined quantitatively by oxidizing glucose with glucose oxidase to gluconic acid. The reaction product hydrogen peroxide causes in conjunction with a peroxidase, such as horseradish peroxidase, the conversion of a substrate, i. e. an indicator, into a chromogenic product, which is detectable and relates proportional to the glucose concentration in the sample fluid.

Measuring the glucose concentration in samples of whole blood is a particularly common task. Since Diabetes causes dangerous physiological complications leading to the loss of vision, kidney failure and other serious medical consequences. Only a stringent therapy and disease management minimises the risk of these consequences with adjustments on exercise, diet, and medication. Some patients have to test their blood glucose concentration frequently with four or more measurements a day. These patients as well as clinicians and hospitals require an accurate, reliable, and ideally inexpensive method to adjust their treatment regimes to avoid the long-term complications of diabetes mellitus.

The increased awareness about diabetes, the acceptance of self-monitoring and self-treatment have been dependent upon the availability of suitable devices and let to the development of a multitude of devices and methods for personal use and point of care testing as well. Available are pregnancy, ovulations, blood coagulation, ketone and cholesterol tests, as example for a non-exhaustive selection, but most prominent in the area of self-monitoring is still the detection of glucose in capillary blood.

An exemplary device for monitoring the concentration of an analyte, e. g. glucose, in blood is disclosed in the U.S. Pat. No. 4,935,346. The method involves taking a reflectance reading from the surface of an inert porous matrix impregnated with a reagent that will interact with the analyte to produce a light-absorbing reaction product. Most of the devices of the prior art are designed to have one measurement area or measurement chamber in which the test sample is introduced directly or via a fluidic path or channel, the test chamber or test membrane contains all materials necessary for the reactions, which produce a detectable colour change of the sample fluid.

U.S. Pat. No. 5,430,542 discloses a disposable optical cuvette and method of manufacturing. The cuvette comprises two optically transparent liquid impermeable plastic sheets. A third adhesive sheet is positioned between the two transparent plastic sheets and all three sheets are pressed and sealed together.

U.S. Pat. No. 5,268,146 discloses a qualitative test panel for testing a sample for the presence of an analyte containing all reagents and components necessary to achieve a visible indication of the presence or absence of an analyte in the sample.

U.S. Pat. Nos. 4,761,381 and 5,997,817 disclose devices wherein the liquid samples to be analysed are applied to sample application ports which give the liquid entry to capillary channels leading to reaction chambers which contain material capable of detecting the components of interest in the liquids.

U.S. patent application Publications US 2002/0110486A1 and US 2003/0031594 A1 disclose fluidic medical diagnostic devices permitting the measurement of analyte concentration or a property of a biological fluid, particularly the coagulation time of blood, the devices having at one end a sample port for introducing a sample and at the other end a bladder for drawing the sample via a channel to a measurement area, in which a physical parameter of the sample is measured and related to the analyte concentration or property of the fluid.

Due to raw material and process variations in large-scale manufacture of these strips an adequate strip-to-strip reproducibility from one batch to the next is not guaranteed. Therefore, it is necessary to assign a calibration code to each lot of strips that corrects for this vanability. The calibration code may be marked on the strip container, and the user must enter the code into the meter when a new batch of strips is used. If the user fails to enter a new calibration code or enters an incorrect one, the resulting measurement will be incorrect. Some prior art strips, e. g. the strip disclosed in U.S. Pat. No. 6,168,957B1, are designed to incorporate the calibration code on the strip, thus the meter can read the calibration code before calculating the glucose concentration. The disposable nature of single use diagnostic strips allow only destructive testing, due to the consumption of reagents during the determination step, and thus permit only a statistical evaluation of the batch performance by the manufacturer, which does not give 100% certainty of the performance of an individual test strip.

More importantly, these types of calibration codes convey only retrospective information to the analytical strip-reading device or meter. Thus, a meter cannot assess the true history of a particular reagent test strip, e. g. incorrect storage conditions or faulty packaging, and will generate an error message only if the strip provides completely erroneous and off scale readings in comparison to the pre-program data or validation methods.

The user can only check and proof the accuracy and functionality of a reagent test strip with specially prepared control solutions of known concentrations provided by the manufacturer. Nevertheless, this method is also disadvantageous, since the quality check leads to increased strip consumption and therefore to increased costs. Likewise, this method does not take into consideration the quality variations within a batch.

Some of the devices of the prior art have integrated positive and/or negative controls, which are activated by the addition of the sample. For instance, in the above mentioned U.S. Pat. No. 5,268,146 preferred embodiments of the test device include a built-in positive control and/or a built-in negative control which consist of further measuring areas containing reagents which will either induce the visible change in the indicator by themselves or prevent the change from occurring independently of the presence or absence of the analyte in the test sample. Also, the test device of the U.S. Pat. No. 4,578,358 for detecting the presence of occult blood in bodily substances includes positive and negative control areas.

An integrated positive or negative control as disclosed in the above two patents and known commonly from pregnancy tests provides only useful information in conjunction with qualitative and threshold test panels or strips indicating the presence or absence of an analyte but is meaningless for the quality assurance of quantitative determination of analytes such as glucose in whole blood.

Furthermore, the measuring procedure may be impaired by other variable factors in the physiological sample fluid. A typical complication in whole blood analysis is the variability of erythrocyte levels, leading to results which may not reflect the real analyte concentration of the sample.

In view of the aforementioned shortcomings, it is the object of the present invention to provide a device which has an integrated calibration system, which accounts for and compensates any variability may it be generated by fluctuations in the production process or by the variability of the analysed sample itself to assure the user that the test has been properly performed and the result is accurate and reliable.

So far, no dry reagent test strip with integrated calibration system has been disclosed by prior art, but a variety of prior art publications describes test strips with pluralities of reactions zones used to detect a plurality of analytes or to integrate positive or negative controls as indicated above.

A particular interesting prior art test strip comprising a plurality of reaction zones utilised for quality assurance purposes but not for a strip internal calibration procedure has been disclosed in U.S. patent application Publications US 2002/0110486A1 and US 2003/0031594 A1. The test strip requires a volume of about 20 µL blood and is used to determine the prothrombin time, an important parameter to characterise blood coagulation. However, if a user has to test several times a day, as required for proper management of diabetes mellitus, these large sample volumes are unpractical and disadvantageous especially in comparison with the state of the art blood glucose systems which require only about 1 µL of whole blood but require in all events a patient performed calibration procedure as well.

A reduction of the volume of the channels and cavities forming the measuring cavities in the described strip would require complex and expensive production procedures, such as "micro-moulding", which are less suitable for large-scale production of inexpensive and disposable sensors.

Accordingly, it is a further object of the present invention to provide an analyte test system for dry reagent test strips, which requires not only small volumes of physiological or aqueous fluid but also a production process which does not involve many and complicated production steps and therefore is inexpensive and usable for products assisting patients in self-monitoring blood glucose or other important physiological parameters.

SUMMARY OF THE INVENTION

This invention provides a device for determining the concentration of an analyte like glucose, cholesterol, free fatty acids, triglycerides, proteins, ketones, phenylalanine or enzymes, in a physiological fluid like blood, serum, plasma, saliva, urine, interstitial and/or intra-cellular fluid, the device having an integrated calibration and quality control system suitable for dry reagent test strips with a very small sample volume of about 0.5 µL based on to a new sample distribution system. The production of the inventive analyte test element involves only a small number of uncomplicated production steps enabling an inexpensive production of the strips.

Due to the integrated calibration procedure the analyte test system of the present invention provides reliable results regardless of the blood type, haematocrit level, temperature etc. In addition, production variations are compensated by the integrated calibration procedure as well. Moreover, active component aging is now detectable and can be compensated and/or reported which will lead to a prolonged shelf life of the product under suitable storage conditions.

The present invention provides an analyte test element for determining the concentration of at least one analyte in a physiological or aqueous sample fluid having a first and a second surface in a predetermined distance opposite from each other, said both surfaces are provided with two substantially equivalent patterns forming areas of high and low surface energy which are aligned mostly congruent to create a sample distribution system with at least two detection areas, wherein the applied physiological or aqueous fluid is constrained to the areas with high surface energy.

The sample distribution system contained in the inner part of the analyte test element has no mechanical and/or structural features resembling walls, groves, or channels to handle and manipulate the physiological fluid or other aqueous sample fluids. The analyte test element is described in several embodiments suitable for a variety of calibration procedures and adaptable to different analytes and chemical determination methods; it is easily integrated in test strips used for a single measurement or in more complex arrangements such as analyte test disks or bandoliers to provide base units for several measurements.

In a preferred embodiment, the analyte test element provides n predetermined detection areas of said first surface coated with a catalytic formulation promoting the detection of an analyte in a physiological or aqueous fluid, and n predetermined detection areas of said second surface coated with n calibration formulations made up of m blank formulations and n-m formulations with different levels of calibration compound, whereby n is an integer number larger than 2, m is an integer number equal or larger than 1, and n>m, configured proximal to the centre of the analyte test element, enabling the detection means to obtain n results from 2n predetermined detection areas and subsequently allowing a processing means to calculate n-m calibration coefficients of a polynomial calibration equation obeying $$y = \sum_{1}^{n-1} \{c_{(n-1)} x^{(n-1)}\},$$

one regression coefficient to validate the quality of the calculated n-m calibration coefficients of the calibration equation, and the determination of the unknown concentration of an analyte in a physiological or aqueous fluid sample.

In another aspect, the invention provides a method for preparing the analyte test element of the present invention with the steps:

generating areas of high and low surface energy on a base layer having a first surface, the areas of high surface energy forming a hydrophilic pathway with n predetermined detection areas, whereby n is an integer number larger than 2, generating a corresponding pattern of areas of high and low surface energy on a cover layer having a second surface, coating a catalytic formulation on the n detection areas of the first surface, said catalytic formulation promoting the detection of an analyte concentration contained in a physiological or aqueous fluid sample using transmission or absorbance photometry, coating n calibration formulations on n detection areas of the second surface, said n calibration formulations made up of m blank formulations and n-m formulations with different levels of calibration compound, whereby m is an integer number of at least 1, and n>m, which is identical or substantially equivalent to the analyte and able to induce the same chemical reaction in the catalytic formulation as the analyte in the physiological or aqueous-fluid sample, laminating the layers of first and second surfaces to the opposite sites of a centre layer having a discontinuity which provides a cavity for the sample distribution system formed by the areas of high surface energy on the first and second surfaces of the base and cover layer, punching or cutting the laminated sheets to the final shape.

Other features and advantages of the present invention and the preferred embodiment thereof will become apparent from the following description in conjunction with the attached drawings.

BRIEF DESCRIPTION OF THE DRAWINGS

FIG. 4 shows different forms of the discontinuity of the centre layer forming the sample cavity together with the first and second surface.

FIG. 7 shows different embodiments of the sample distribution system with different patterns of pathways and detection areas suitable for different calibration methods.

FIG. 11 shows different shapes of the analyte test strip.

Figure 5A:
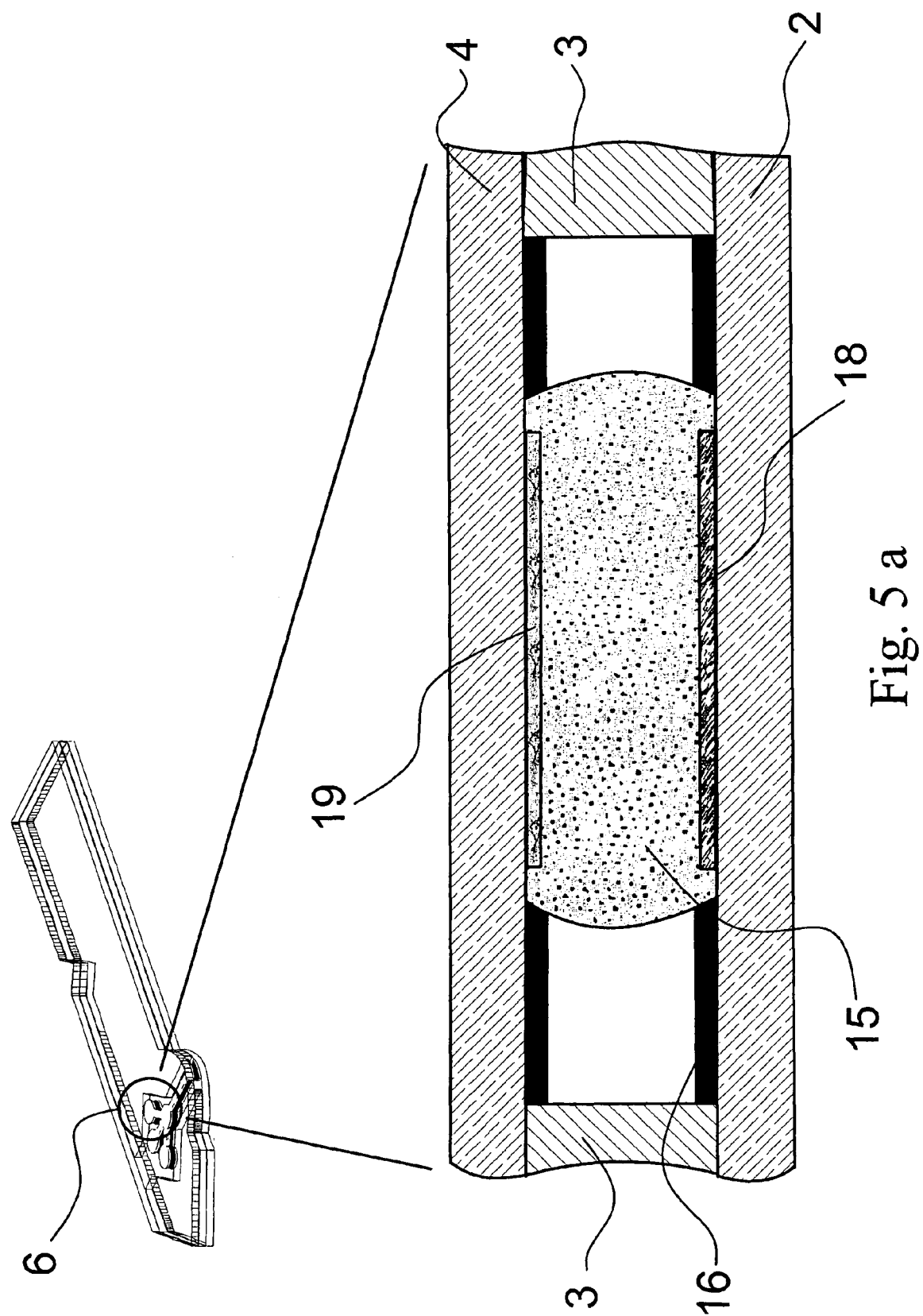
FIG. 5a is a sectional view of a detection area of the sample distribution system constructed by hydrophobic guiding elements.
Figure 6:
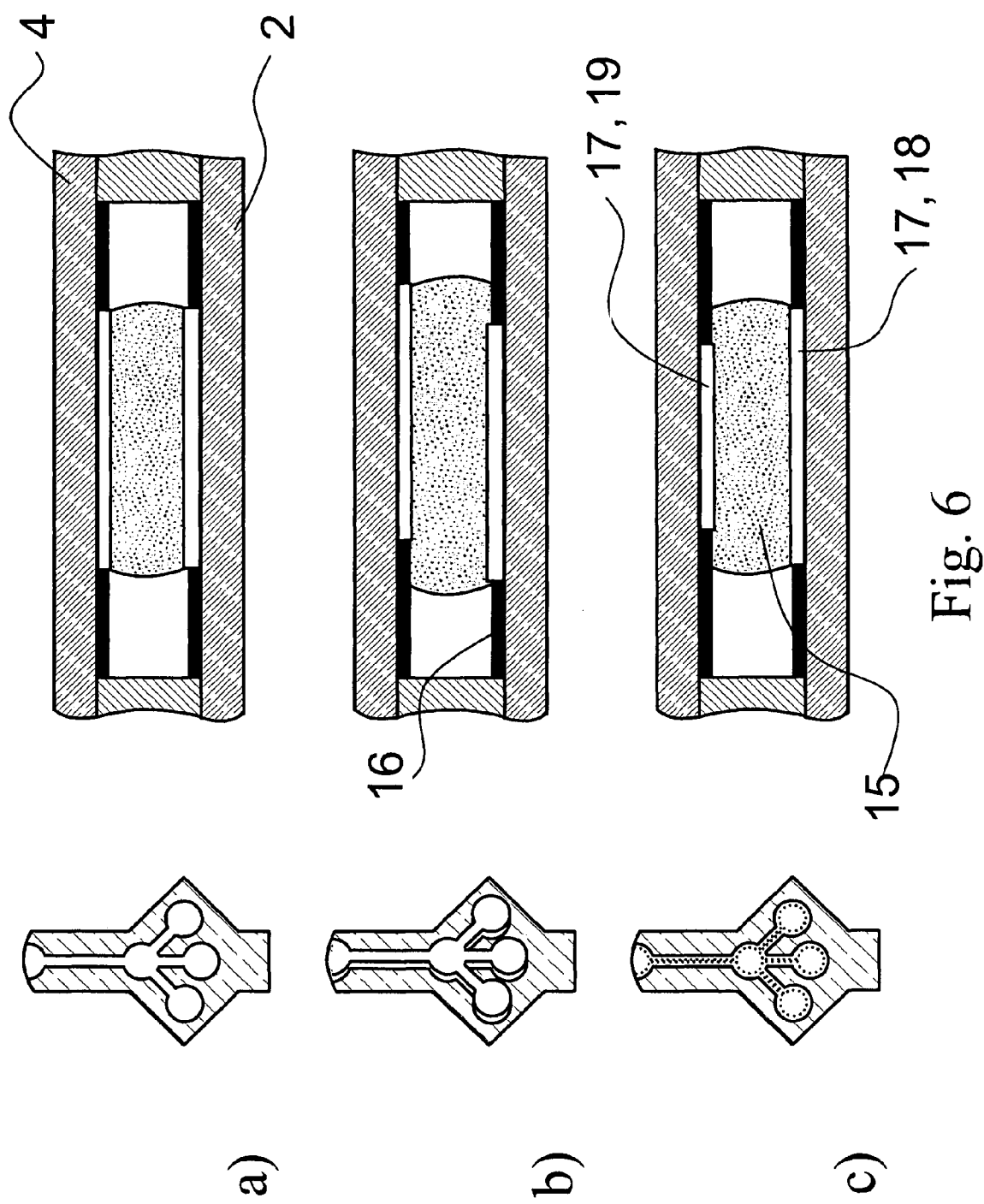
FIG. 6 shows the influence of registration failures during the lamination process on the sample volume of the analyte test element and the top respectively the sectional view of an alternative embodiment, which allows higher tolerances for the registration of base and cover layer without compromising on the test strip quality.
Figure 8:
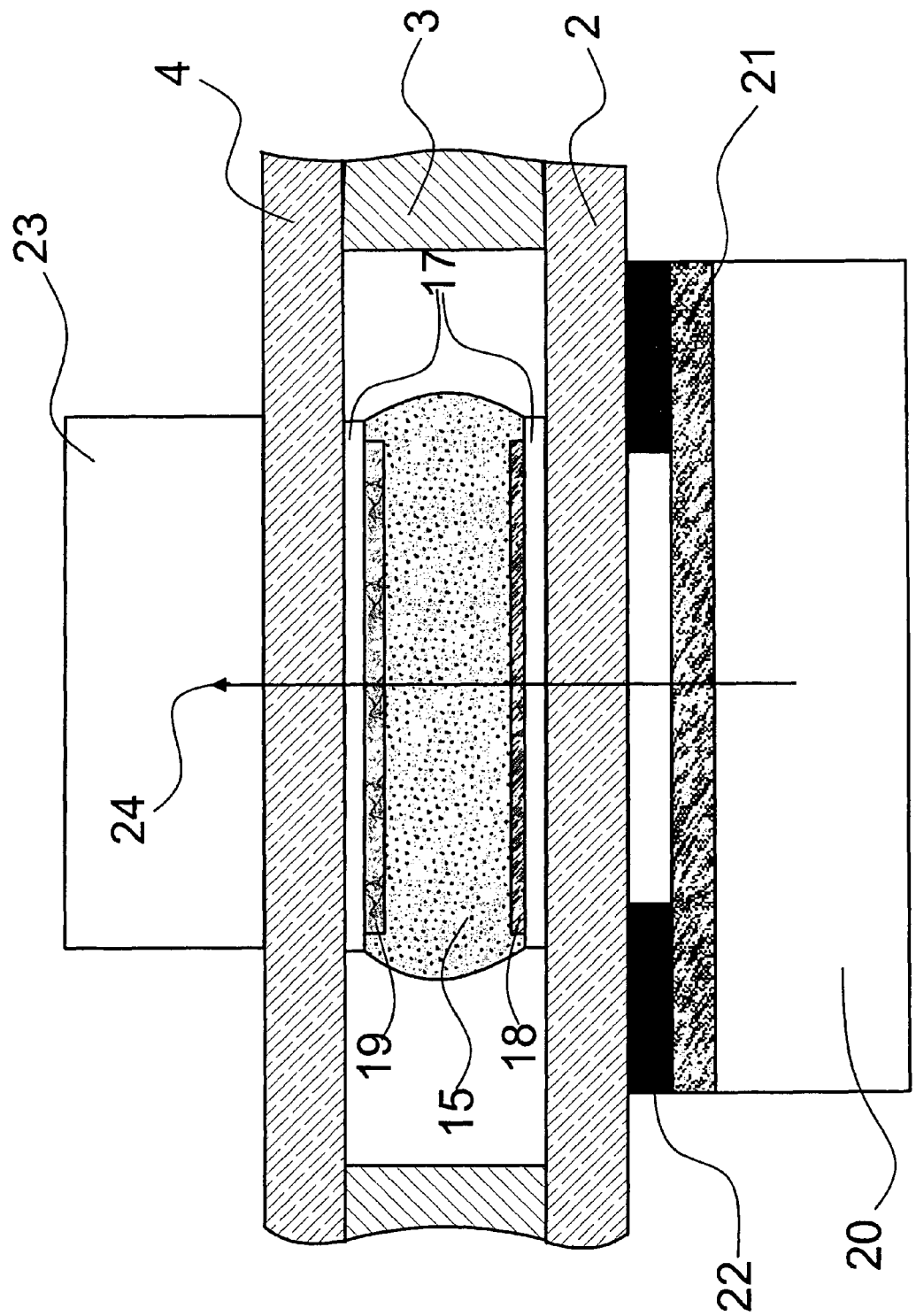
FIG. 8 shows the sample distribution system of FIG. 5b in conjunction with a light emitter and detector means in a sectional view.

The layers shown in FIGS. 5a, 6, and 8 are not to scale, in particular the thickness of the layers 16, 17, 18, 19 are largely exaggerated.

DETAILED DESCRIPTION OF THE INVENTION

Figure 1:
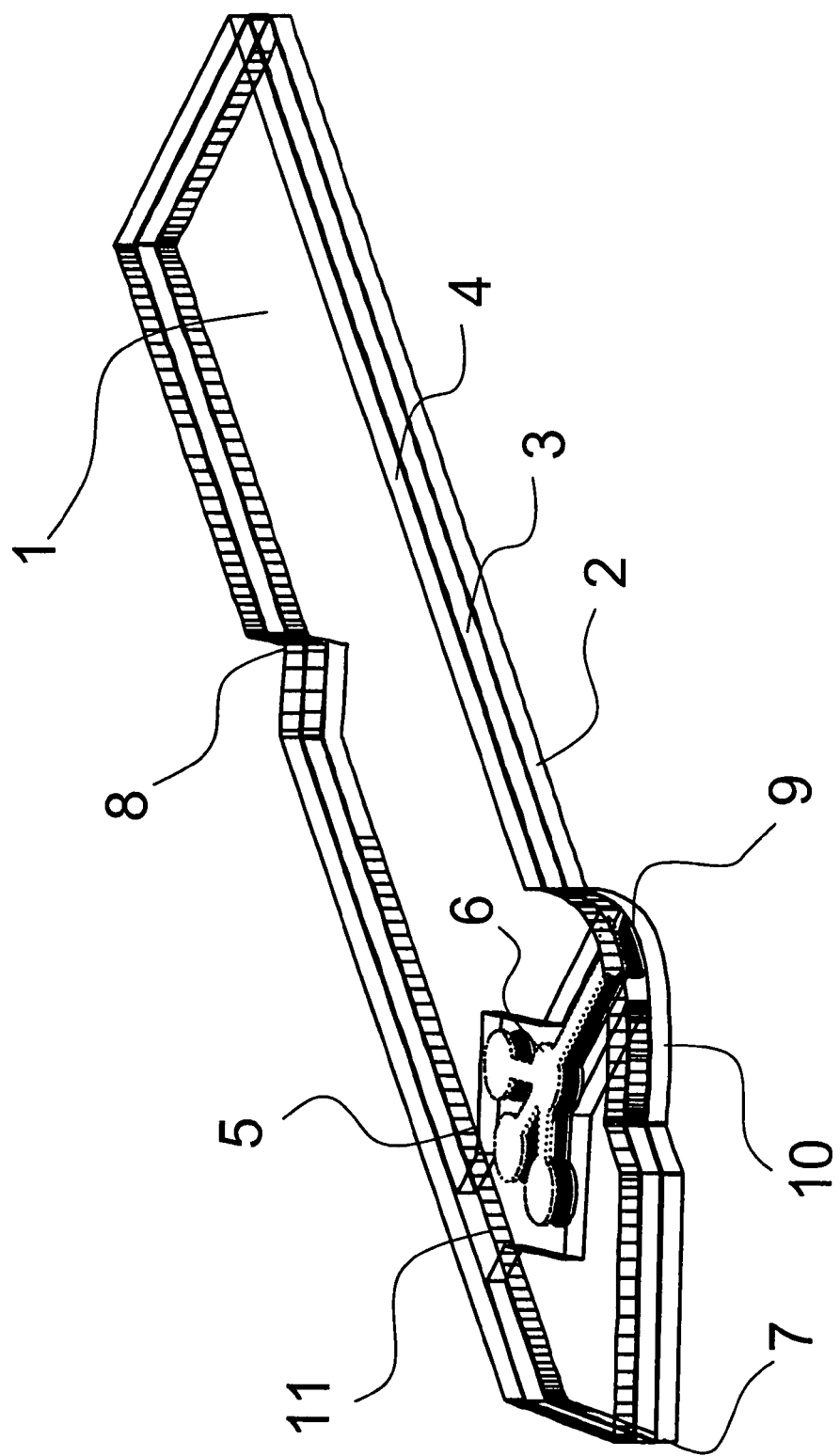
FIG. 1 is a perspective view of one embodiment of the analyte test element of the present invention provided in shape of a test strip.
Figure 2:
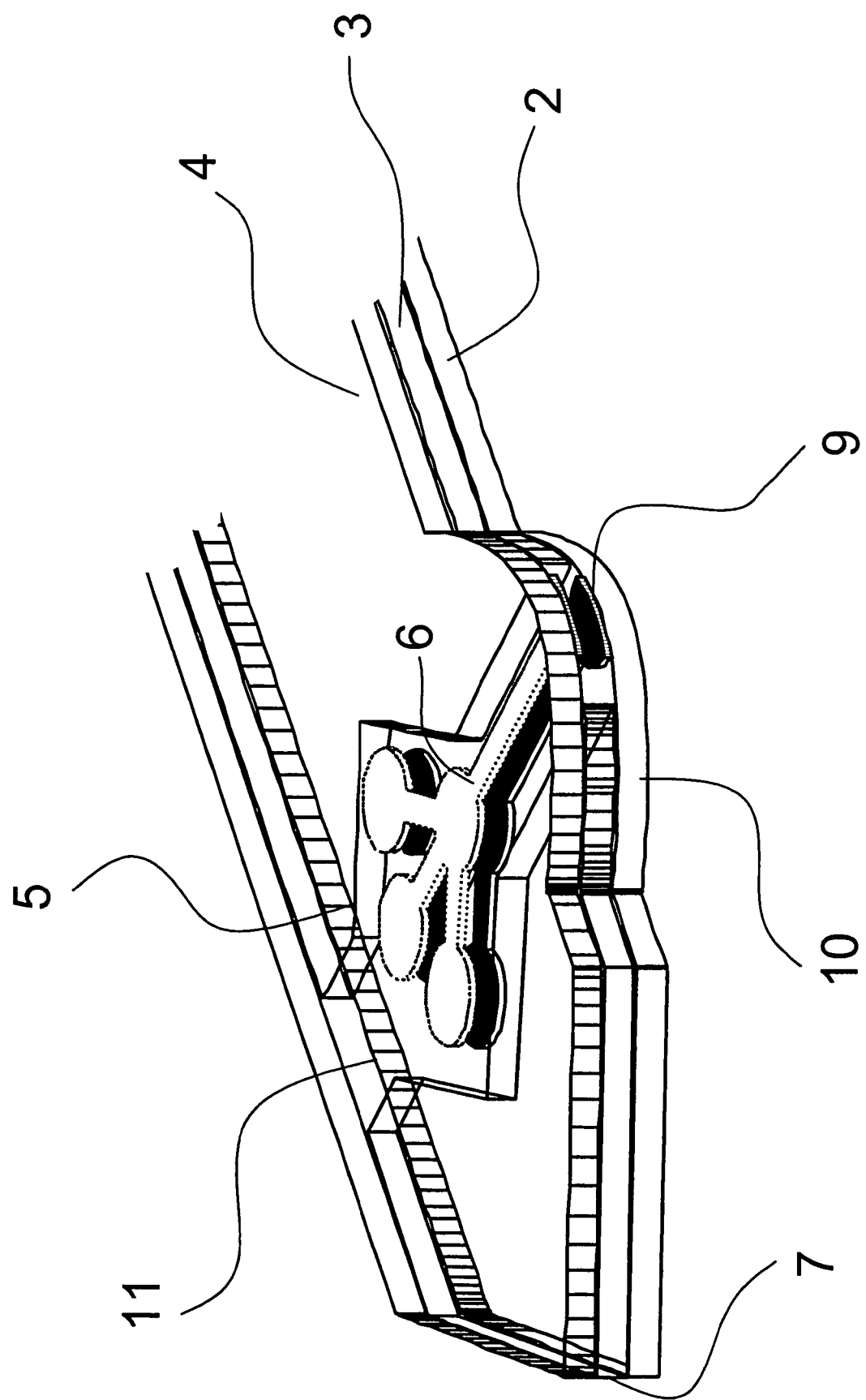
FIG. 2 is a perspective view of the embodiment according to FIG. 1, showing the sample distribution system enlarged.

As shown in FIG. 1 and FIG. 2, the analyte test strip 1 of the present invention is a multiple layer arrangement comprising a base layer 2, a centre layer 3 overlaying the base layer 2, and a cover layer 4 overlaying the centre layer 3. The centre layer 3 presents a discontinuity 5, which creates a hollow cavity in conjunction with the base layer 2 and the cover layer 4. Within said cavity there is located a sample distribution system 6 which is connected to a sample application area 9 located on one side of the analyte test strip. The sample application area 9 as interface to the user is preferably formed by a convex curve 10 extending from one major side of the analyte test strip for easier application of the sample. Opposite to the sample application area 9, 10 on the second major side of the analyte test strip is the location of an air vent 11 allowing the displacement of air while the physiological or aqueous fluid is distributed to the predetermined detection areas 6a, 6'a (see FIG. 3). It might be noted that the construction requires only one air vent independent of the amount of predetermined detection areas used within the analyte test element. The described elements of the sample distribution system with areas of high surface energy, sample application area, air vent, centre layer and discontinuity in the centre layer form the totality of the analyte test element, which creates the intrinsic capillary action to exert the distribution of the applied physiological or aqueous fluid to the predetermined detection areas.

Figure 3:
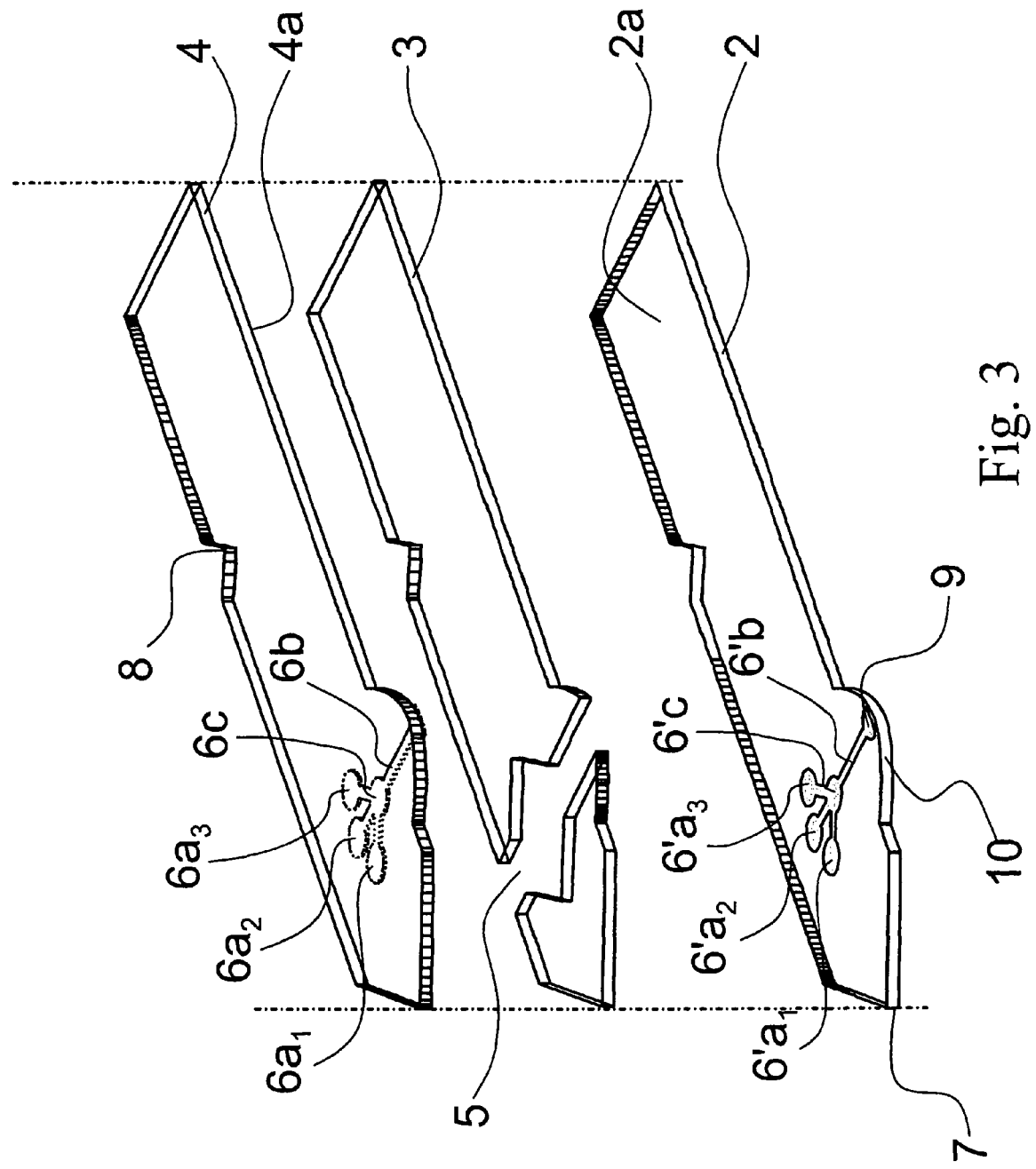
FIG. 3 is an exploded perspective view of the device according to FIG. 1 showing the three layers separately.

In addition, the analyte test strip 1 possesses registration features 7, 8 useful to differentiate between several kinds of analyte test strips for the determination of different analytes. By this means, a multi-analyte meter could be instructed to run a special program or procedures with selectable parameters upon strip insertion required for the determination of a particular analyte. As illustrated in FIG. 3, which represents the multi-layer arrangement of FIG. 1 and 2 in an exploded view, the base layer 2 provides a first surface 2a, and the cover layer 4 provides a second surface 4a. The first surface 2a and the second surface 4a are patterned with areas which will create the sample distribution system 6. The pattern of the sample distribution system 6 comprises a predetermined number of analyte detection areas 6a and sample pathways 6b, which are aligned and registered mostly congruent upon assembly of the multi-layer arrangement. The centre layer 3 defines the distance between the first surface 2a of the base layer 2 and the second surface 4a of the cover layer 4 and has a discontinuity 5 to form a hollow cavity together with the first surface 2a of the base layer 2 and the second surface 4a of the cover layer 4. The sample distribution system 6 which will be formed between the first surface 2a and second surface 4a is located within the cavity created by the discontinuity 5 of the centre layer 3 and the first surface 2a of the base layer 2 and the second surface 4a of the cover layer 4. Preferably, the hollow cavity is substantially larger by design than the sample distribution system.

Since the purpose of the discontinuity 5 of the centre layer is only to create a cavity for the sample distribution system 6, the discontinuity 5 of the centre layer 3 can have different forms, examples thereof are shown in FIG. 4. FIG. 4a shows an umbrella shaped analyte test element cavity 12, FIG. 4b shows a rectangular analyte test element cavity 13, and in FIG. 4c the sample cavity 14 has a circular shape. The discontinuity 5 of the centre layer 3 does not influence the size of the predetermined detection areas 6a and the size of the pathways 6b of the sample distribution system 6 and therefore does not influence or change the required sample volume. Compared to the sample distribution system 6, the cavity shapes shown in FIG. 4 are rather simple, thus allowing the application of simple punch tools and fast processing with less demand on the registration accuracy.

The sample distribution system 6 located in the cavity formed by the discontinuity 5 of the centre layer 3 and the first surface 2a of the base layer 2 and the second surface 4a of the cover layer 4 is formed by creating areas of high and low surface energy on said surfaces 2a and 4a. The areas of high and low surface energy on the first surface 2a of the base layer 2 and the second surface 4a of the cover layer 4 are aligned and registered mostly congruent to each other. Since the applied physiological fluid or any other aqueous sample is wetting only the areas with high surface energy, it is thus constrained within the predetermined flow paths 6b and detection areas 6a of the sample distribution system 6 and between the first surface 2a of the base layer 2 and the second surface 4a of the cover layer 4.

FIG. 5a shows a construction of the sample distribution system 6 using hydrophobic "guiding elements". In this embodiment of the analyte test element of the present invention the base layer 2 and the cover layer 4 are coated with a hydrophobic layer 16, except the areas, which will form the sample pathways and detection areas. The hydrophobic layer 16 creates an area with low surface energy, which will exert a repellent force onto an applied sample fluid and constrain the sample fluid therefore to the areas of high surface energy which will form the sample distribution system.

Preferably, the hydrophobic layer 16 is applied on a hydrophilic surface, which is wettable by the physiological or aqueous fluid and transparent for light, particular in the UV, near IR, and/or visible range of the electromagnetic spectrum. The procedure described above requires a hydrophilic surface, which can be produced from a natural hydrophilic polymer such as cellophane or glass as well as from a hydrophobic surfaces of common polymers (examples are given below) by rendering the hydrophobic surface hydrophilic using a coating process or physical or chemical plasma deposition of hydrophilic monomers that can be vaporised in vacuum, e. g. ethylene oxide, ethylene glycol, pyrrole or acrylic acid. Subsequently, the pattern of "guiding elements" can be realized by printing hydrophobic ink on the hydrophilic surfaces of the base and cover layers.

A suitable hydrophobic ink will have contact angles with water of typically more than 70° and a surface energy of typically less than 33 mN/m and contain monomers, oligomers, and pre-polymers with hydrophobic functions, like isooctyl acrylates, dodecyl acrylates, styrene derivates, or systems with partly fluorinated carbon chains.

FIG. 5b shows another construction of the sample distribution system using hydrophilic pathways. In this embodiment of the analyte test element the base layer 2 and the cover layer 4 are coated with a hydrophilic layer 17 thereby creating areas of high surface energy.

The hydrophilic agent printed on the hydrophobic surface is highly wettable by a physiological or aqueous fluid; thus, the areas of high surface energy creating the hydrophilic pathways of the sample distribution system will exert a positive capillary force onto the applied physiological or aqueous sample fluid to transport the sample fluid to the separate detection areas.

The hydrophilic pattern can be realized by printing a cross-linkable and/or partly insoluble hydrophilic or amphiphilic agent on a hydrophobic surface. Inks with hydrophilic functions can be realised from a wide selection of cross-linkable water-soluble polymers, particularly useful are acrylate derivatives prepared form polyalcohols, polyethylene-glycols, polyethylene-oxides, vinylpyrolidone, alkyl-phosphocholine derivates and others; particularly useful are also organo-modified silicone acrylates, which are a cross-linkable species of organo-modified polysiloxanes. Suitable coatings provide a contact angle with water of typically less than 25° and a surface energy of typically more than 70 mN/m.

The base layer 2 and cover layer 4 suitable as substrate for the printing process may be formed of a material like glass, polyvinyl acetate, poly-methyl-methacrylate, poly-dimethyl-siloxane, polyesters and polyester resins containing fluorene rings, polycarbonates and polycarbonate-polystyrene graft copolymers, terminal modified polycarbonates, polyolefins, cycloolefins and cycloolefin copolymers, and/or olefin-maleimide copolymers.

In case the substrate has an intermediate hydrophobic character, the printing of hydrophilic pathways with a surrounding hydrophobic pattern, i. e., a combination of the constructions of FIG. 5a and FIG. 5b, is possible as well.

In an alternative embodiment, either the first or second surface is provided with the hydrophilic/hydrophobic pattern (6, 14) whereas the corresponding surface provides a homogeneous pattern of hydrophilic pixels surrounded by a hydrophobic area thereby creating a surface with semi hydrophilic and semi hydrophobic character (amphiphilic character), which eliminating the necessity to align the hydrophilic and hydrophobic pattern (6, 14) of the first surface with an equivalent hydrophilic and hydrophobic patern (6', 14') of the second surface. The properties of such an amphiphilic surface can be easily designed by the geometric pattern of the hydrophilic pixels and the overall ratio between the hydrophilic and the hydrophobic area. In the disclosed invention the amphiphilic character, respectively the ration between hydrophilic pixels and hydrophobic areas, is designed that the sample fluid progresses from hydrophilic pixel to hydrophilic pixel only if the opposite surface provides hydrophilic character. If the opposite surface provides hydrophobic character the movement of the fluid within the capillary gap of the analyte test element will stop. This mechanism allows the above-described method to form a functional analyte test element without the stringent requirement of precise registration of the corresponding pattern of the sample distribution system provided on the first and second surface.

However, preferably both the first and the second surface are provided with equivalent patterns of high and low surface energy to ensure a quick distribution of the sample fluid within the hydrophilic pathways of the sample distribution system.

Moreover, it is possible to physically elevate the areas of high surface energy of first and second surfaces from the areas of low surface energy by etching, embossing, or simply by printing the hydrophilic layer (17) with about three to five times increased thickness on the first and the second surface. Due to this elevation the capillary gap of the hydrophilic pathways gets smaller in relation to the surrounding area and exerts a higher capillary forth on the sample liquid.

The volume requirement for the sample distribution system contained in the analyte test element of the preferred embodiment is with about 0.5 µL-1.0 µL very low and requires only about 100 nL-150 nL per detection area, whether the areas of high and low surface energy are created by hydrophobic guiding elements or hydrophilic pathways or by a combination of both. However, it will be obvious for the one skilled in the art that the volume of the sample distribution system will vary with various designs and with the number of employed predetermined detection areas.

As stated above, the creation of a sample distribution system with such volume including a plurality of sample distribution pathways and detection areas is very difficult or even impossible with prior art test strip technology. The amount of physiological sample needed for a measurement in the analyte test element of the present invention is e. g. as low as 1/40 part of the amount which is required for the operation of the device disclosed by Shartel et al. in U.S. patent application Publications US 2002/0110486A1 and US 2003/0031594A1 and e. g. 1/10 of the volume of prior art micro-cuvettes (HemoCue Glucose Systems).

Figure 7:
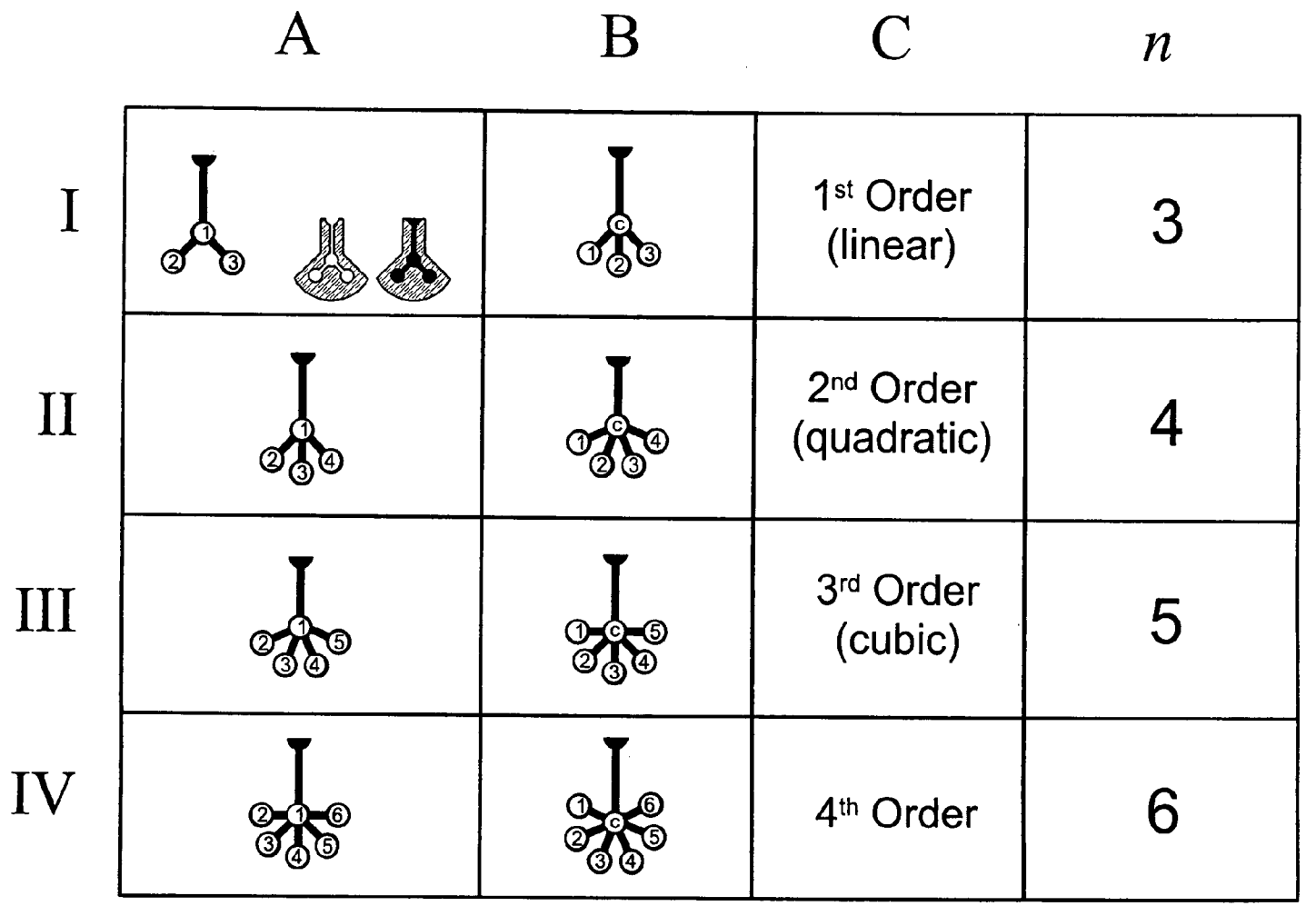
Figure 9:
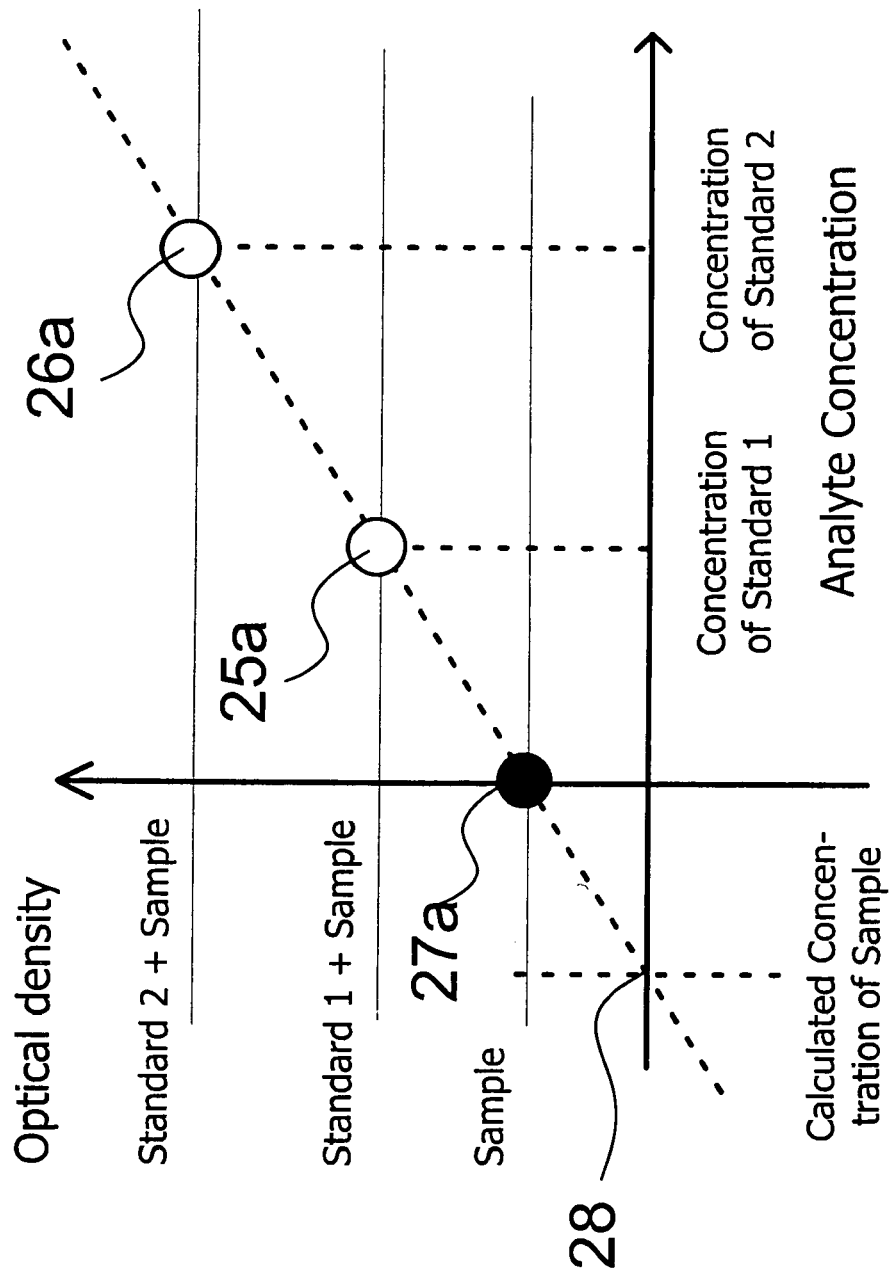
FIG. 9 is a graph showing the calculation of the sample analyte concentration using the standard addition method.

FIG. 7 shows different patterns of the sample distribution system, which can be realized by hydrophilic pathways as illustrated in FIG. 5b, or by the hydrophobic "guiding elements" as illustrated in FIG. 5a, or by a combination of hydrophilic pathways and hydrophobic guiding elements. Cell AI in FIG. 7 illustrates all cases for the simplest sample distribution system. Column A of FIG. 7 shows the formal design of sample distribution systems with no background correction, whereas column B provides designs for sample distribution systems with background corrections, column C indicates the highest order of the polynomial calibration equation achievable with the adjacent designs, and column n indicates the required number of predetermined detection areas of each surface, respectively the number of required measurements. The literals in each design indicate the position of the background correction (c), sample (1), and all associated calibration areas (2, 3, 4, 5, 6) with increasing amount of calibration compound. The simplest calibration is represented by a linear equation where the relationship between measurement and the analyte concentration is strictly proportional. The calibration of the analyte test element is generally performed using the standard addition method by adding the calibration compound of the different calibration areas to the sample and subsequent calculation of a linear or monotone non-linear calibration equation. FIG. 9 gives a more detailed explanation about case I. The calibration model or order (column C) needs to be appropriate for the selected analyte and employed detection chemistry, consequently it is not possible to apply a linear calibration model to a chemical reaction which obeys a fourth order model and vice versa. However, it is still possible to use the analyte test element designed for five standard additions for a linear calibration, the higher amount of standards will allow an even more precise measurement and a statistical validation with higher significance in terms of correlation coefficient, standard deviation and standard error of the test compared to a linear calibration based on two standards.

Moreover, the repetition of sample and standard measurements is possible as well, thus it is possible to perform two independent linear calibrations for one particular sample of physiological or aqueous fluid with the embodiments shown in row IV. Likewise, it is possible to use the same analyte test element for the determination of two analytes.

On the contrary, a multi analyte system can be realised within the same set of predetermined detection areas if the selected detection chemistries generates no interference problems, thus the reaction educts and products of one reaction will not take part in the other reaction and the produced indicator dye absorbs the light in a substantially different wave length range.

Figure 5:
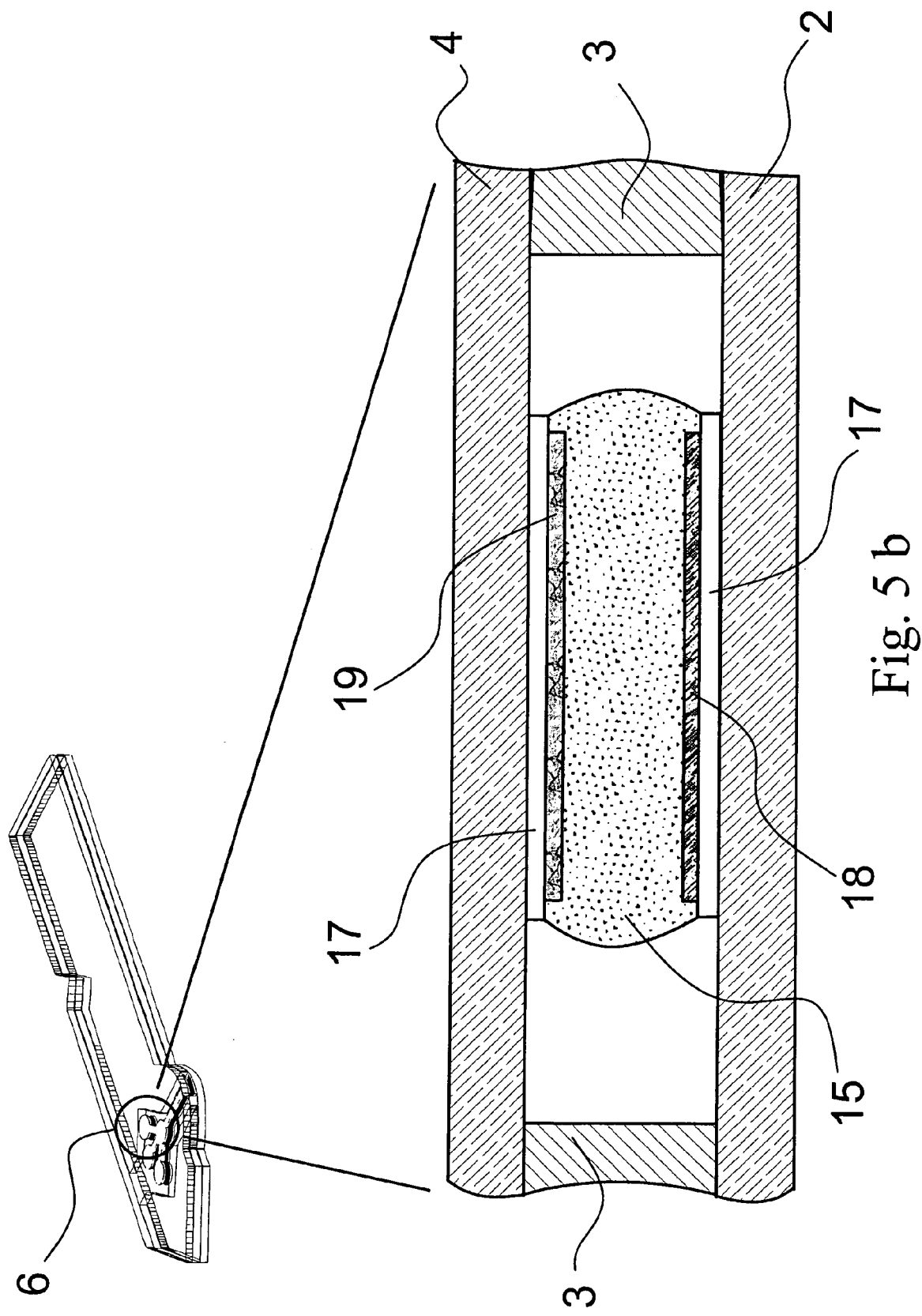
FIG. 5b is a sectional view of another embodiment of a detection area of the sample distribution system using hydrophilic pathways.

Referring to FIG. 3, the analyte detection areas $6'a$ of the sample distribution system 6 of the first surface $2a$ of the base layer 2 are characterized in that they are coated with a catalytic formulation 18, as shown in FIGS. 5 and 6. The catalytic formulation 18 contains as reactive components a promoter undergoing a catalytic or non-catalytic reaction with the analyte, if necessary, in conjunction with a co-enzyme, and an indicator generating an optically detectable product, thus allowing the detection of the analyte contained in sample 15 by transmission or absorbance photometry.

Preferably, the promoter is an enzyme selected from the group consisting of dehydrogenases, kinases, oxidases, phosphatases, reductases and/or transferases. The optional co-enzyme contained in the catalytic formulation is a substance required by certain enzymes to facilitate the enzymatic reaction, 3-nicotineamide adenine dinucleotide is required for example by glucose dehydrogenase.

In one assay system for determining concentration of glucose, glucose in the sample is oxidized by oxygen and glucose oxidase to form gluconic acid and $H_2O_2$. The amount of $H_2O_2$ produced is then measured quantitatively by Reaction (1) or Reaction (2).

Reaction (1):

$$\text{Dye (colourless)} + H_2O_2 \xrightarrow{POD} \text{Oxidized dye (coloured)} + H_2O$$

Reaction (2):

$$H_2O_2 + Fe^{2+} \longrightarrow Fe^{3+} + H_2O$$

$$Fe^{3+} + \text{dye-} \longrightarrow Fe^{3+} \text{ dye complex}$$

In Reaction (1), the enzyme peroxidase (e. g., horseradish peroxidase, microperoxidase) catalyzes the oxidation of the dye and converts $H_2O_2$ to $H_2O$. The colour intensity is directly proportional to the concentration of glucose in the sample. Representative examples of dyes include o-dianisidine, 4-aminoantipyrine, and 3,3',5,5'-tetramethybenzidine. In Reaction (2), $H_2O_2$ oxidizes the $Fe^{2+}$ to $Fe^{3+}$. $Fe^{3+}$ forms a coloured chelate complex with a specific absorption peak. Representative examples of ferrous salt include ferrous sulphate and potassium ferrocyanide. Representative examples of the chelate-dye include xylenol orange. The amount of formed $Fe^3$+chelate complex is proportional to the amount of glucose in the sample.

In another assay used to determine glucose concentrations in physiological fluids is shown in Reaction (3); here glucose dehydrogenase (GDH) reacts specifically with glucose in the sample in presence of a co-enzyme (3-nicotinamide adenine dinucleotide (3-NAD)) to form NADH, the reduced form of 3-NAD. The NADH reacts subsequently with an electron accepting dye, e. g., 3-[4,5-dimethylthiazol-2-yl]-2,5-diphenyltetrazolium bromide (MTI), catalyzed by the diaphorase enzyme to form a dark purple-reddish colour. The colour intensity measured at 640 nm is directly proportional to the concentration of glucose in the sample.

Reaction (3):

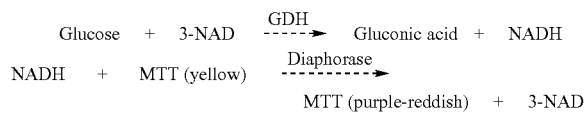

An alternative strain to wild-type GDH is glucose dehydrogenase pyrroloquinolinequinone (GDH-PQQ) which is often used for electrochemical blood glucose determination but could be employed in an optical detection method using indicator dyes formed by reduction similar to the MTT or by chelate complexes indicators as shown in the later half of reaction scheme (2).

Though, the catalytic formulation 18 may contain glucose oxidase or glucose dehydrogenase if the device is intended for the determination of glucose concentration in a physiological fluid.

Accordingly, the enzyme contained in the catalytic formulation may be cholesterol oxidase, where the analyte is cholesterol; alcohol oxidase, where the analyte is alcohol; lactate oxidase, where the analyte is lactate, and the like.

Indicators suitable to generate an optically detectable product by itself or in combination with another chemical compounds and in conjunction with a suitable promoter, e. g. an enzyme, are preferably selected from the group consisting of aromatic amines, aromatic alcohols, azines, benzidines, hydrazones, aminoantipyrines, conjugated amines, conjugated alcohols, and aromatic and aliphatic aldehydes. Specific examples of the indicator include 3-methyl-2-benzothiazolinone hydrazone hydrochloride; 3-methyl-2-(sulfonyl)-benzothiazolone hydrazone hydrochloride (MBTH); 8-amino-1-napthol-5,7-disulfonic acid (Chicago acid); 3,3', 5,5'-Tetramethylbenzidine (TMB); 4,5-dihydroxy-2,7-napthalene-disulfonic acid; 1-hydroxy-2-naphthalene-sulfonic acid; N,N-dimethyl-aniline; o-tolidine; 3-dimethyl-aminobenzoic acid (DMAB); 2,2'-Azino-bis(3-ethylbenzothiazohne-6-sulfonic acid) diammonium salt (ABTS); 3-[4,5-dimethylthiazol-2-yl]-2,5-diphenyltetrazolium bromide (MTT); and/or 3,5-dichloro-2-hydroxybenzene-sulfonic acid. In case the chemical compound is an acid, a water-soluble salt of the acid, e. g. an ammonium salt, may be used in the preparation of the catalytic formulation.

A variety of enzyme inks suitable as catalytic formulation is available from prior art publications e. g. Wong et al. (U.S. Pat. No. 6,312,888), Philips et al. (U.S. Pat. No. 4,935,346), and Berti et al. (U.S. Pat. No. 4,247,297). Suitable catalytic formulations for the present invention are based on a non-reactive base, indicator components (dyes), and an enzyme or enzyme combinations as promoter. The non-reactive base provides a carrier, which needs to be suitable for the coating process, preferably ink jet printing, enzyme stabilisation, and fixation of the enzyme and indicator system to the surface of the detection areas. An exemplary composition for 100 mL formulation is given below.

| Non-reactive base: | | |
|---|---|---|
| Distilled water | 65 ml | |
| Citric acid | 2.4 g | Buffer system |
| Sodium citrate · $2H_2O$ | 3.2 g | Buffer system |
| Polyethylene glycole | 1.0 g | Crust inhibitor |
| N-Methylpyrolidone | 2.0 g | Co-solvent for some indicator dyes (optional) |
| BAS | 3.0 g | Enzyme stabilization |
| Gafquat 440 (ISP) | 1.0 mL | Film forming agent |
| Advantage S (ISP) | 1.0 g | Film forming agent |
| PVA (low mol. weight) | 1.5 g | Enzyme stabilization |
| Adjust pH to 6.5 and fill up to 100 mL | | |

| Catalytic formulation: (all components are added to 100 mL non-reactive base) | | |
|---|---|---|
| | GOD (Aspergillus niger) | 2.0 g (250 U/mL) |
| | POD (Horseradish) | 2.0 g (250 U/mL) |
| Indicator system a) | TMB | 0.801 g |
| Indicator system b) | ABTS | 0.915 g |
| Indicator system c) | MBTH | 0.719 g |
| | DMBA | 0.551 g |
| Indicator system d) | MBTH | 0.359 g |
| | Chicago acid | 1.064 g |

The catalytic formulation can be composed with the indicator systems a) to d) in combination with a variety of hydrogen peroxide producing enzymes such as GOD. Albeit, the pH of the non-reactive base formulation needs to be adjusted to the requirements of a new enzyme if GOD is replaced by another catalyst.

Examples for non-enzyme catalysed reactions are the detection of albumin with tetrabromphenol blue and the detection of ketones with a phosphate buffered mixture of glycine and nitroprusside in the visible range of the electromagnetic spectrum.

If the analyte test element is designed to perform n determinations, whereby n is an integer number larger than 2, all of the n detection areas 6'a on the first surface are coated with the catalytic formulation 18 promoting the detection of the analyte in the physiologic sample.

Referring again to FIGS. 3, 5 and 6, the detection areas 6a of the second surface 4a of the cover layer 4 are characterized in that they are coated with a calibration formulation 19 comprising a calibration compound.

Preferably, the calibration compound contained in the calibration formulation 19 coated on the predetermined detection areas 6a of second surface 4a is identical or substantially equivalent to the analyte and able to induce the same chemical reaction in the catalytic formulation as the analyte in the physiological fluid sample. In case the analyte of interest in the physiological sample is glucose then the calibration compound is preferably glucose as well.

The non-reactive base as described for the catalytic formulation is suitable for the calibration formulation as well and requires only the addition of the required levels of calibration compound. N-Methylpyrolidone, a co-solvent required for some of the indicator dyes, can be omitted.

An exact dosing of the calibration compound applied to the different detection areas is critical for a proper calibration procedure and thus for a reliable calculation of the analyte concentration in the sample fluid. Therefore, as the catalytic formulation, also the calibration formulation is preferably coated on the predetermined detection areas by ink jet printing. By that means it is possible to dose exactly the amount of the calibration compound and to apply it on a specific detection area.

If the analyte test element is designed to perform n determinations, whereby n is the number of determinations without repetitions or background measurements, which represents an integer number larger than 2, then n predetermined detection areas on the second surface $4a$ are coated with the n calibration formulations made up of n-m formulations with different levels of calibration compound or analyte and m blank formulations, whereby m is an integer number of at least 1, and n>m. In other words, at least one of the n detection areas of the sample distribution system does not contain the calibration compound to allow the determination of the analyte concentration.

After the physiological fluid is applied to the sample application area and distributed to the predetermined detection areas by capillary action, it dissolves the catalytic formulations on the n predetermined detection areas of the first surface $2a$ as well as the n calibration formulations on the n predetermined detection areas of the second surface $4a$ forming a mixture of analyte, calibration compound (which may be additional analyte), promoter and indicator dye. Within these n mixtures the optical density is changing proportional to the different levels of calibration compound plus the unknown level of analyte, thus allowing the optical determination of n results by transmission and/or absorbance photometry and the calculation of the analyte concentration. Preferably, the catalytic formulation and the calibration formulations applied to the predetermined detection areas are readily soluble by a physiological fluid and/or water and positioned close to each other to allow rapid diffusive mixing of both components, thus enabling a fast reaction of all components contained in the detection areas to expedite a fast photometric determination of the analyte concentration.

FIG. 8 shows a detector arrangement for measuring the optical density of the sample within the analyte test element according to FIG. $5b$. The arrangement includes a light source 20, which emits light 24 of a certain wave-length in direction of the sample detection area. The light emitted from the light source 20 passes through an optical arrangement 21, e. g. diffuser or lens, and an aperture 22, the base layer 2, the sample 15, and the cover layer 4 of the detection area and is detected on the opposite side of the device by a detector means 23.

Since there are more than two detection areas arranged within the sample distribution system, whereby at least two of the detection areas contain known but different levels of calibration compound it is possible for the processing means to calculate the unknown concentration of the analyte from the n measurements performed with the physiological fluid in the analyte test element.

FIG. 9 shows an exemplary calculation of an analyte concentration in a sample by the linear standard addition method, a known calibration technique used in various fields of analytical chemistry, but now integrated and used with a dry reagent test strip for the first time. In this example, the sample distribution system includes three analyte detection areas, two are coated with different predetermined levels of a calibration compound. After applying the physiological fluid to the sample distribution system, the catalytic reaction takes place in the analyte detection areas, and the light emitter and detection arrangement of the meter measures a first optical absorbance $25a$ of the sample located in the detection area with the first level of calibration compound. The readout of this detection area represents a signal proportional to the combined concentration of the first calibration compound and the concentration of the analyte. In parallel, a second optical absorbance $26a$ is measured of the sample located in the detection area with the second level of calibration compound representing a signal proportional to the combined concentration of the second calibration compound and the concentration of the analyte. Furthermore, a third optical absorbance $27a$ is determined of the detection area containing only the sample with unknown analyte concentration.

Since there is a linear correlation between optical density and concentration of the analyte, following Lambert-Beer's Law, the processing means of the analyte test system can calculate by linear regression analysis of the measurements the coefficients for the calibration equation $y=c_0+c_1 x$ in the example above. The concentration of the analyte in physiological or aqueous fluid sample is determined by the zero point (y=0) 28 of the previously calculated calibration equation.

A general representation of applicable calibration equations is given in form of:

$$y = \sum_{1}^{n-1} \{c_{(n-1)} x^{(n-1)}\}$$

with y =f(results of the optical measurement); x=f(concentration of the calibration compounds); n number of measurements required for the determination without repetitions or background measurements according to FIG. 7A.

This polynomial equation format provides in conjunction with the n-values presented in FIG. 7 the entity of most useful calibration models for the various designs of the sample distribution systems in the aforementioned figure. The values for y and x may represent data calculated by a function to allow pre-processing of raw data generated by the detection mean. Thus, it is possible to use a logarithmic function for linearization of raw data.

It should be obvious from the discussion that the invention is not limited to the designs of sample distribution systems in FIG. 7; and someone skilled in the art becomes able to design a systems with n larger than 6 in conjunction with the provided information.

A detailed introduction in linear and non-linear standard addition methodology is given by Frank et al. (Anal. Chem., Vol. 50, No. 9, August 1978) and Saxberg et al. (Anal. Chem. Vol. 51, No 7, June 1979).

A preferred embodiment of the analyte test element of the present invention according to FIG. 3 is designed to comprise one detection area, which includes the catalytic compounds but no calibration compound ($6a_1$ and $6'a_1$, resp.), one detection area which includes the catalytic compounds and a first concentration of the calibration compound ($6a_2$ and $6'a_2$, resp.), one detection area which includes the catalytic compounds and a second concentration of the calibration compound ($6a_3$ and $6'a_3$, resp.) and one detection area for the background absorption (6c and 6'c, resp.). By means of the latter detection area, which includes neither a calibration compound nor catalytic compounds, it is possible to determine the background absorption of the sample, e.g. haemoglobin in the case of whole blood, and to consider it during the calibration process.

Figure 10:
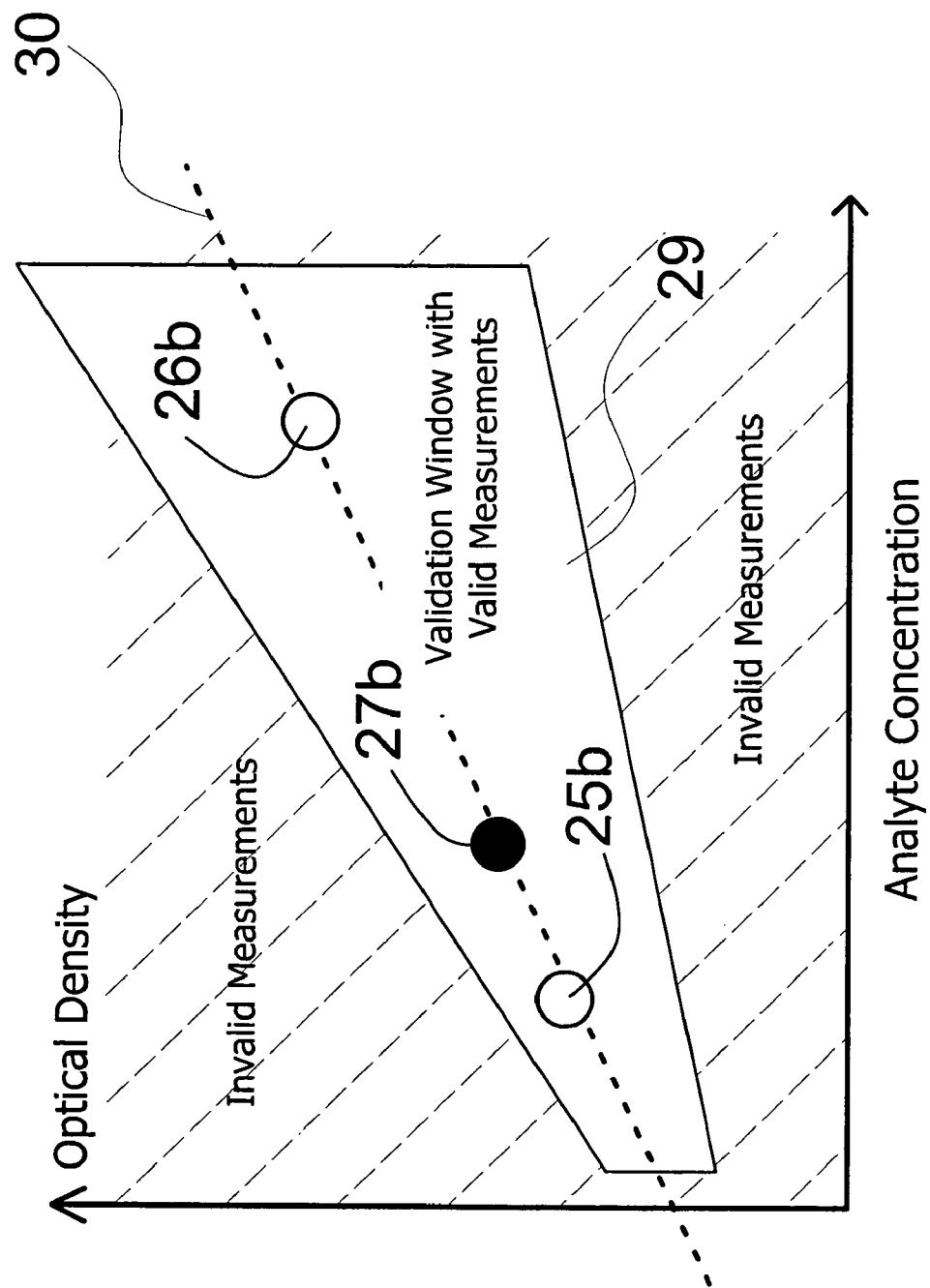
FIG. 10 is a graph showing the validation method for the calculated result and calibration data.

FIG. 10 illustrates a pre-programmed validation method for calculated results and calibration data, whereby the validity of the measured results is verified by defining a "validation window" 29 for valid and correct measurements. By this means, the analyte test system can constrain all data to a validated and useful concentration range, e. g. 30 to 600 mg/dL glucose, and a valid range for the optical density, e. g. 0.1 to 0.9. Likewise, the processing means can constrain the slope and the intercept or more general the coefficients $c_0$ to $c_{(n-1)}$ to a valid range, which is particularly useful for non-linear polynomial equations. A population of valid measurements with a corresponding calibration line located within the boundaries of the validation window 29 is illustrated in FIG. 10; see literals 25b to 27b and 30.

Even more powerful is the validation of results by means of statistical evaluation and linear regression analysis. The quality of the calibration can be judged by a correlation coefficient $r^2$ and a confidence interval, thus the analyte test system can refuse to display a measurement result if the correlation coefficient falls below a pre-programmed threshold. Alternatively, the processing means can calculate a tolerance or concentration range of the result based on the calculated confidence interval. These methods allow a high control over the quality of results provided to the patient, which is used and known today only from sophisticate and expensive laboratory methods and equipment. Even more important for the patient/user is, especially in hospital settings, the quality assurance right at the time of the measurement.

Further security is possible in another embodiment of the present invention; here the analyte test system is configured to relate the concentration of an inert dye to the amount of the calibration compound used in the calibration step. The calibration formulation is composed of the calibration compound and the inert dye with a preset and fixed ratio to each other before it is dosed on the predetermined detection areas of the analyte test element. Thus, the processing means of the analyte test system has the ability to trace and correct for slight variations in the deposited amount of calibration compound if the detector means is configured to determine the concentration of the inert dye with a wave-length different from the wave length used to evaluate the reaction of the indicator compound with the analyte.

Moreover, the manufacturing process control of the dosing and coating step of the calibration formulation become traceable and therefore more reliable. Said inert dye is preferably a water-soluble dye selected from the group consisting of brilliant black BN; brilliant blue G; carmoisine; coumarin 120; direct blue 2B; indigo carmine; new coccine; ponceau 4R; rhodamine 19; sunset yellow; tartrazine; and/or a water soluble derivate of malachite green.

Due to the integrated calibration procedure and validation method, the analyte test system of the present invention provides reliable results by compensating endogenous interferences, such as different blood types and haematocrit levels, as well as exogenous interferences, such as nutrition supplements like Vitamin C or pharmaceuticals, which otherwise would influence and modify the measuring results. Since the calibration of the analyte test system is done in parallel to the measurements, different environmental parameters, such as temperature at the time of actual measurement, are of no consequence for the accuracy of the determined results.

In addition, production variations, e. g. variations in the thickness of the centre layer, are compensated by the integrated calibration procedure and active component aging, e. g., loss of enzyme activity, is traceable and may be compensated which leads then to a prolonged shelf live of the product.

FIG. 11 illustrates different embodiments and shapes of analyte test strips of the present invention adapted to different analyte test systems.

Figure 12:
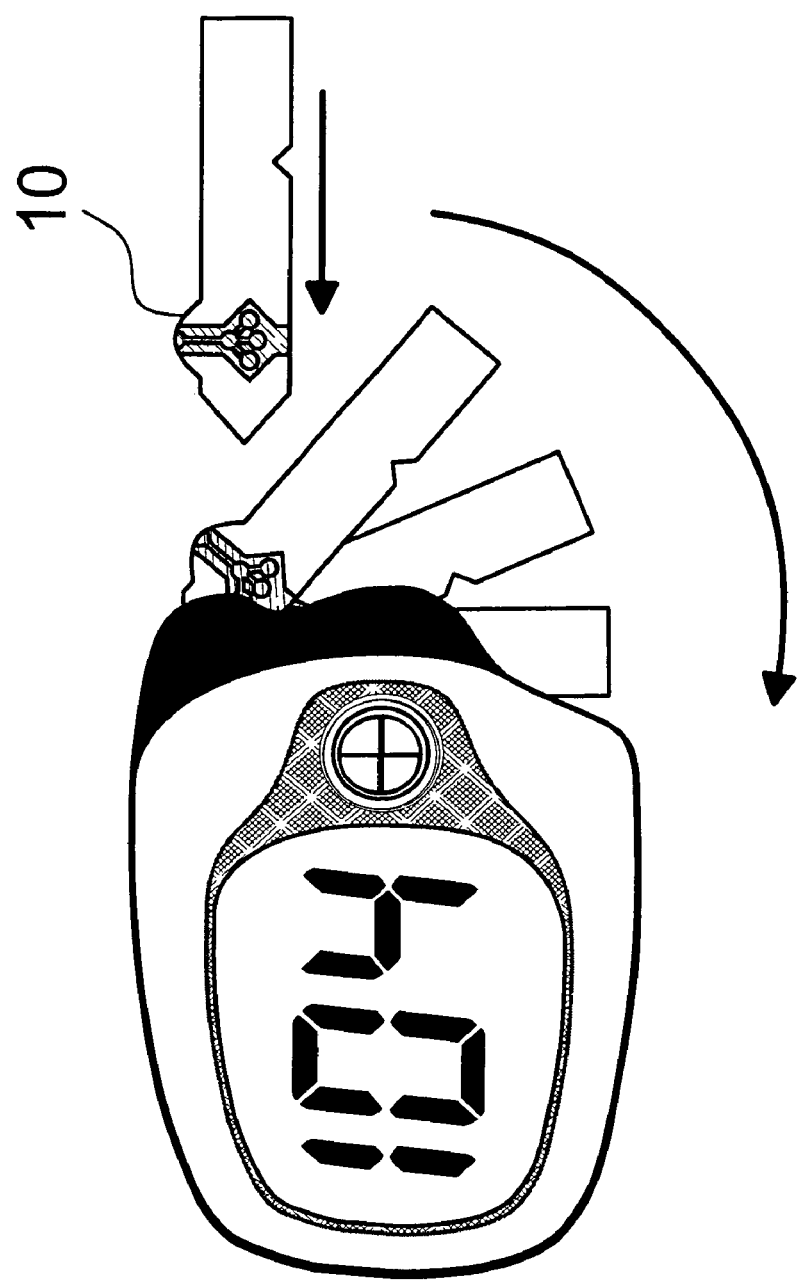
FIG. 12 shows an exemplary application of an inventive test strip with a meter.
Figure 13:
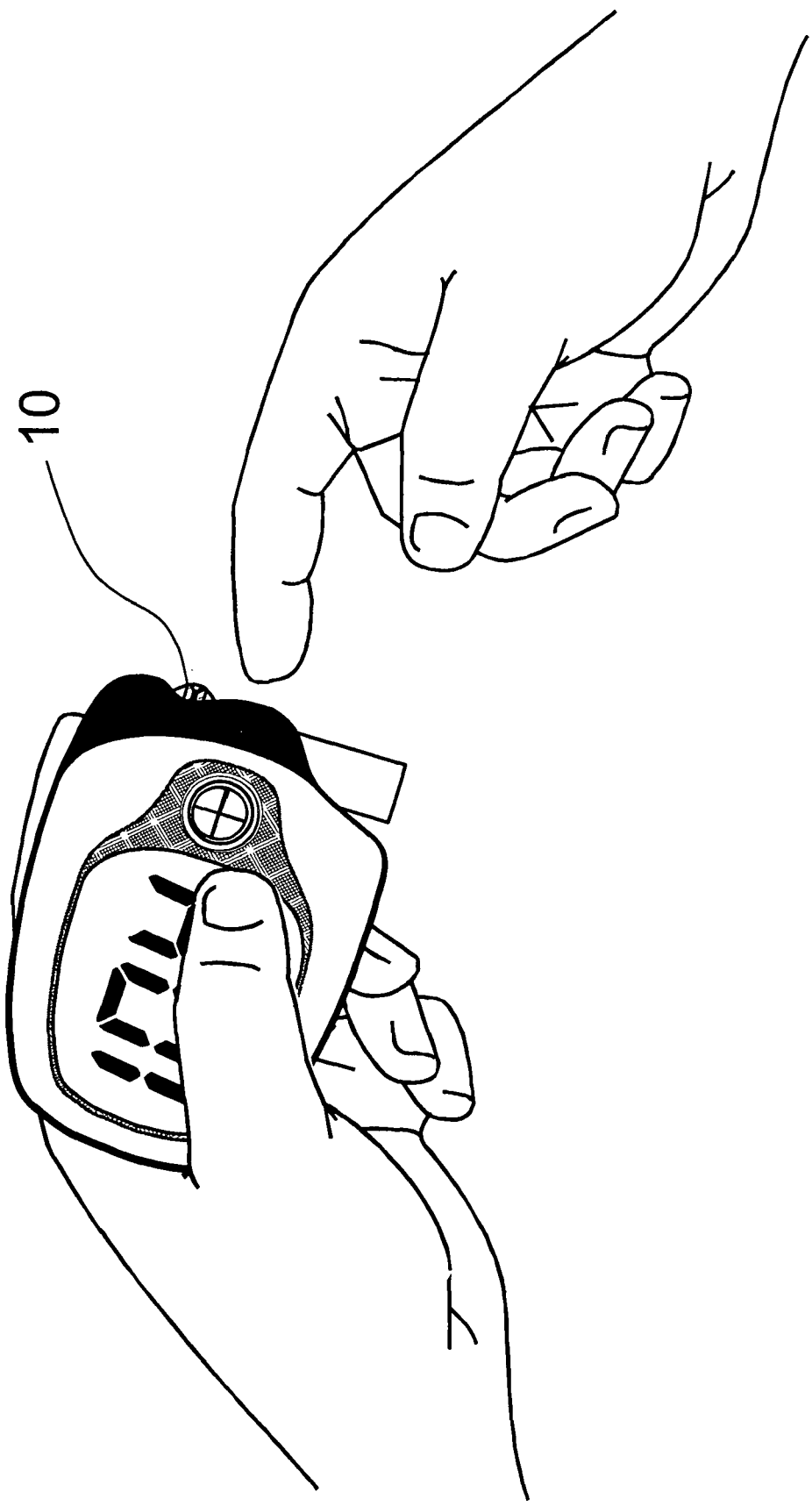
FIG. 13 shows the analyte test system with an inserted analyte test strip.

FIG. 12 shows the insertion of the analyte test strip into an analyte test system. In a preferred embodiment the analyte test strip is designed to have a lateral and concave extension 10 located on one major side of the test strip where the sample application area 9 resides. This feature allows easy application of capillary blood samples from the patients arm or finger as shown in FIG. 13.

Figure 14:
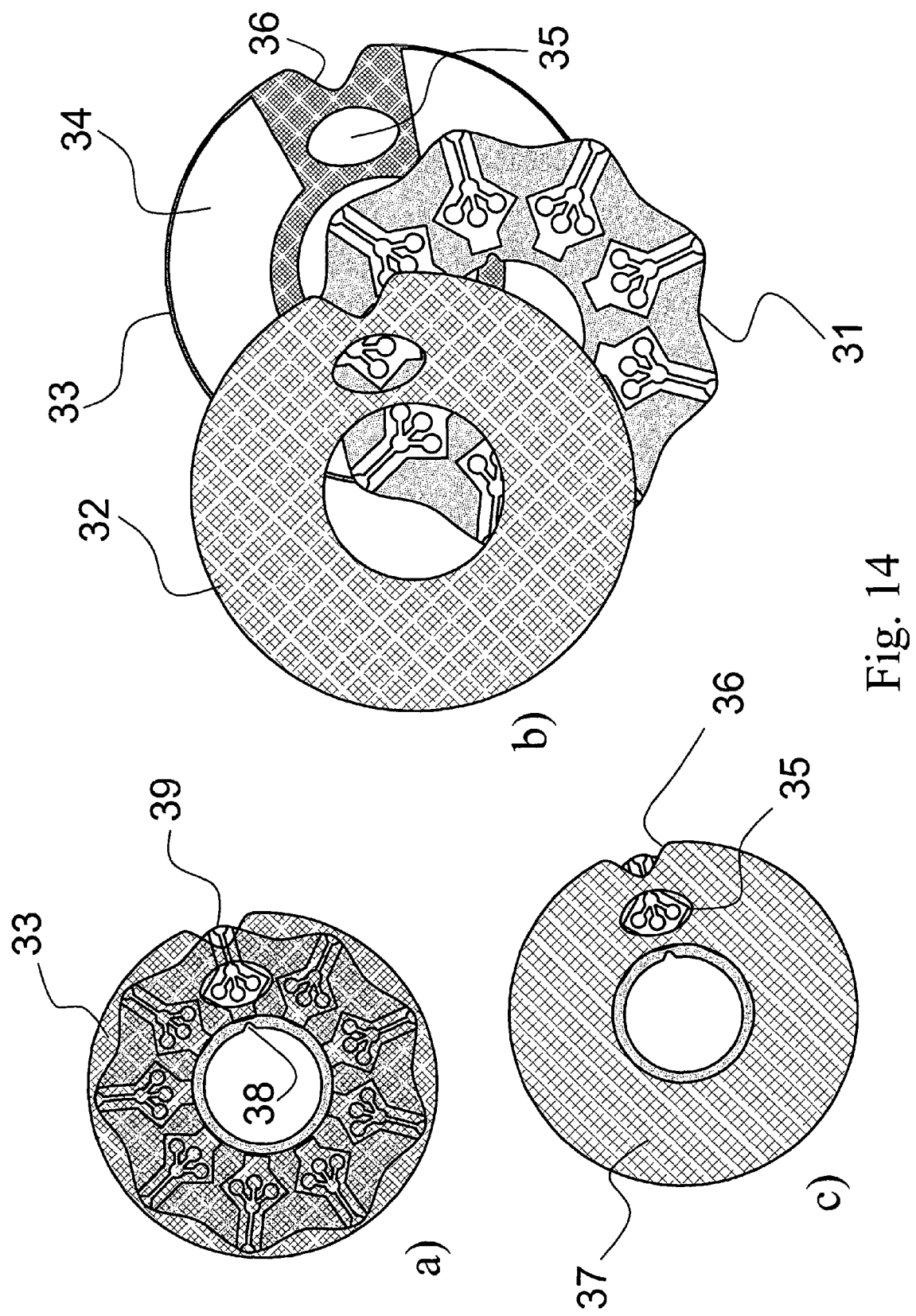
FIG. 14 shows the construction of an analyte test disk.

In another embodiment of the present invention, as shown in FIG. 14, a plurality of analyte test elements is arranged symmetrically around a centre point to form an analyte test disk 31 with outward facing sample application areas 39. The exemplary analyte test disk 31 according to FIG. 14a includes nine analyte test elements of the present invention. As shown in the exploded view of FIG. 14b, the analyte test disk 31 is covered by a disk cover composed of a top layer 32 and a bottom layer 33. The disk cover bottom layer 33 may also be provided with a moisture-absorbing layer 34. The top layer 32 and bottom layer 33 of the disk cover have breakthroughs which are arranged congruently to each other, forming an optical window 35 in which the analyte test element used for the current measurement procedure is located.

Adjacent to the optical window 35 in the outer peripheral areas of the disk cover top layer 32 and the disk cover bottom layer 33 there are provided notches 36 to expose the sample application area 39 of the measurement cell. Preferably, the test disk 31 is additionally provided with a registration notch 38 which may be located in the interior edge of the disk 31. During a measurement procedure, only the analyte test element, which is currently used for the analyte determination is exposed by the optical window, as shown in FIG. 14c. The analyte test disk 31 is able to rotate around its centre point to bring a new analyte test element into position as required.

Figure 15:
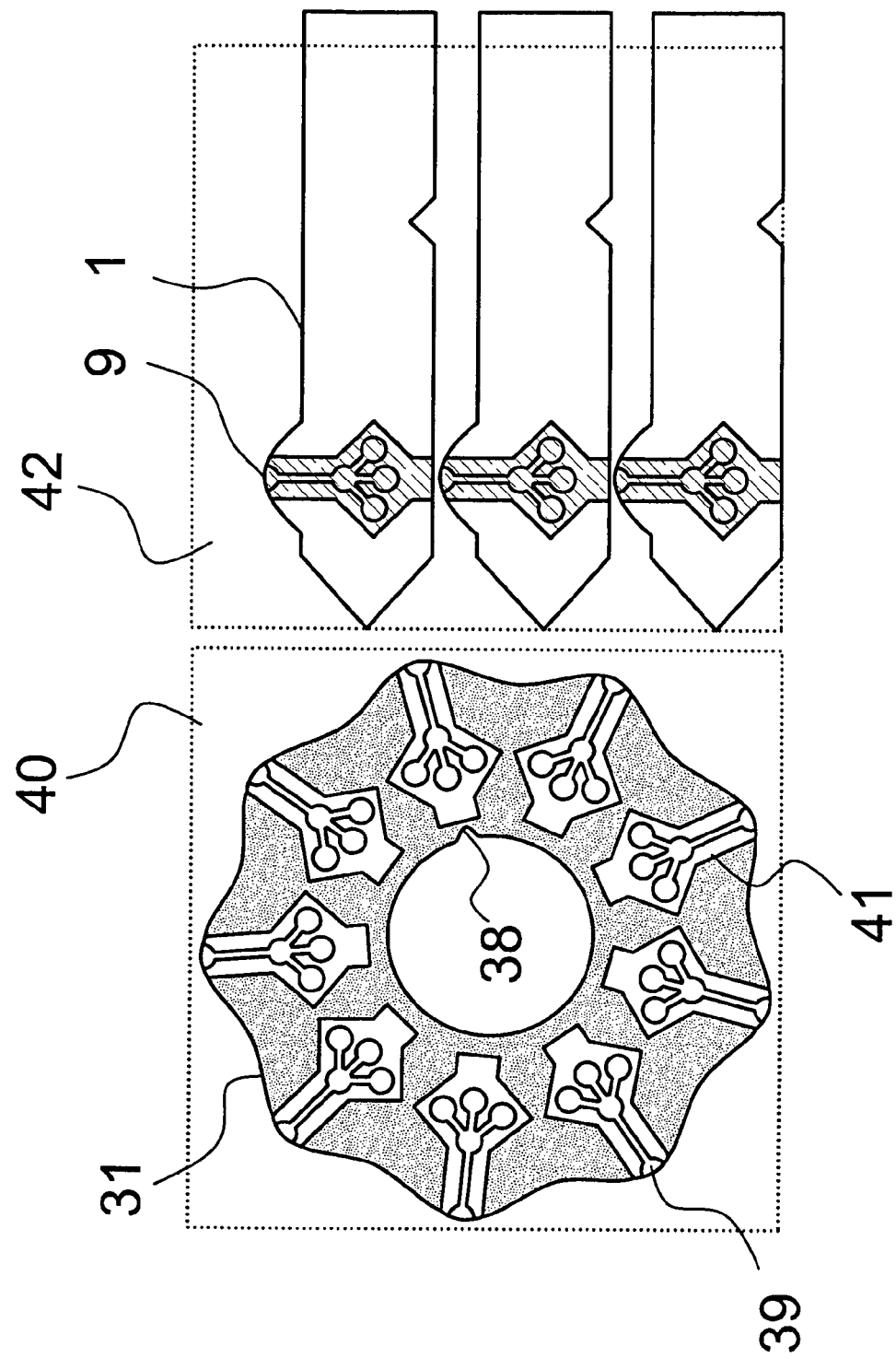
FIG. 15 shows an analyte test disk compared to an analyte test strip.

By means of an analyte test disk, it is possible to arrange a plurality of analyte test elements in a relatively small area. The same number of analyte test elements included in analyte test strips would require a much larger area and thus much more material, as illustrated by the size comparison of analyte test disk and analyte test strips illustrated in FIG. 15. Whereas the unit area 40 of the analyte test disk 31 includes nine analyte test elements 41, the same area 42 would accommodate only three analyte test strips. However, a reduction of the test strip sizes is not possible, because the handling of smaller strips would become difficult and more impractical for the patient.

Figure 16:
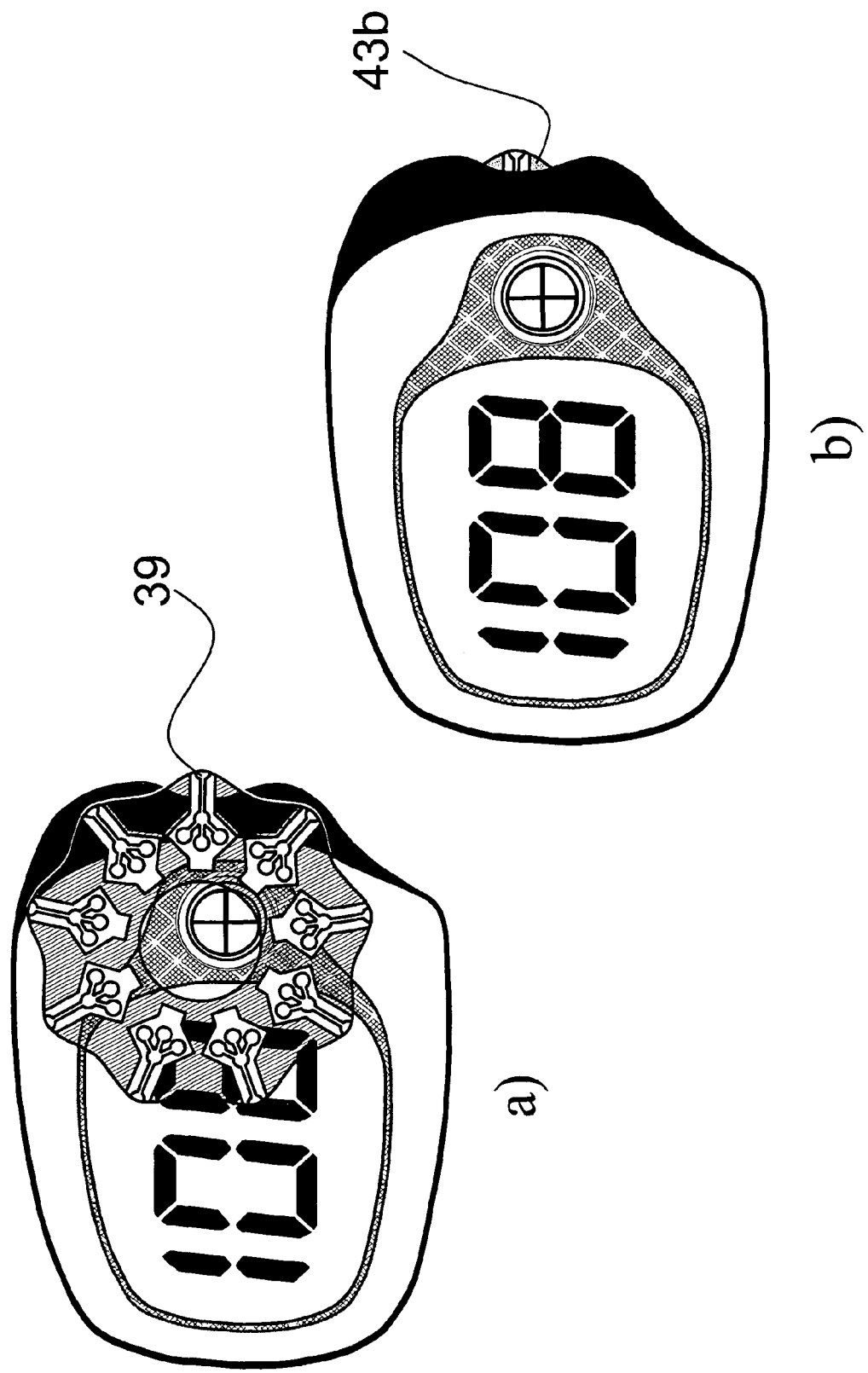
FIG. 16 shows a analyte test system with an integrated analyte test disk.

FIG. 16a and FIG. 16b show the analyte test disk included in a meter, whereby the sample application area 39, 43b again protrudes from the meter housing.

Figure 17:
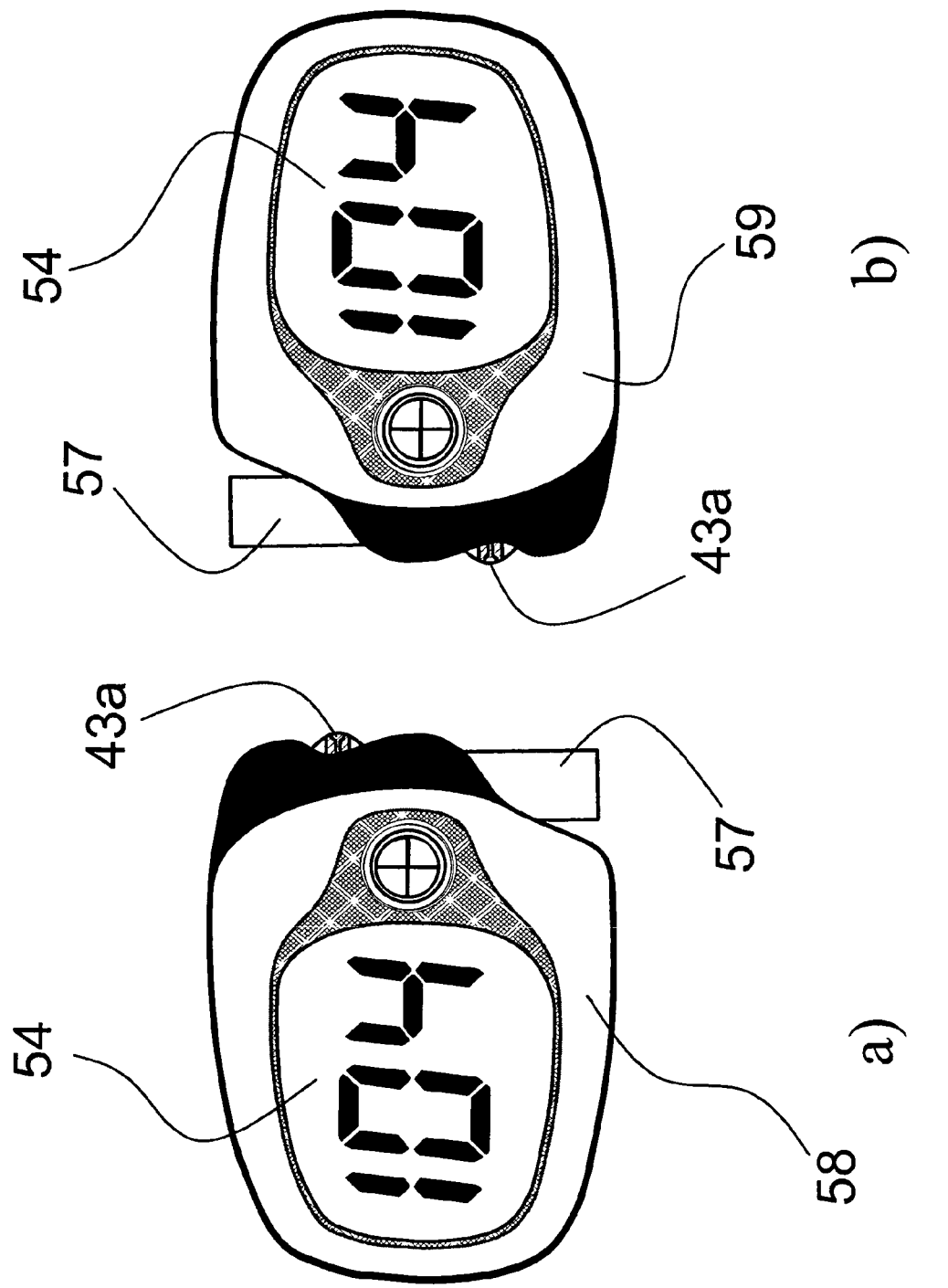
FIG. 17 shows a analyte test system with an analyte test strip in left hand and right hand handling mode.

Not only for the analyte test strips but also for the analyte test disk it is possible to adapt the measurement device (analyte test system) to a left hand and right hand handling mode as illustrated in FIG. 17. When a left hand handling mode is desired according to FIG. 17a, the analyte test strip 57 is inserted into the meter from the bottom side, the sample application area 43*a* for receiving the physiological or aqueous fluid protruding from the meter housing 58. After completion of the measurement, the analyte concentration is presented on the analyte test system display 54. Likewise, a right hand handling mode according to FIG. 17*b* can be realized by adapting the display 54 of the analyte test system 59 to a converse mode of operation by rotating the displayed content on the display by 180°, enabling the insertion of the analyte test strip 57 into the meter from the top side.

Figure 18:
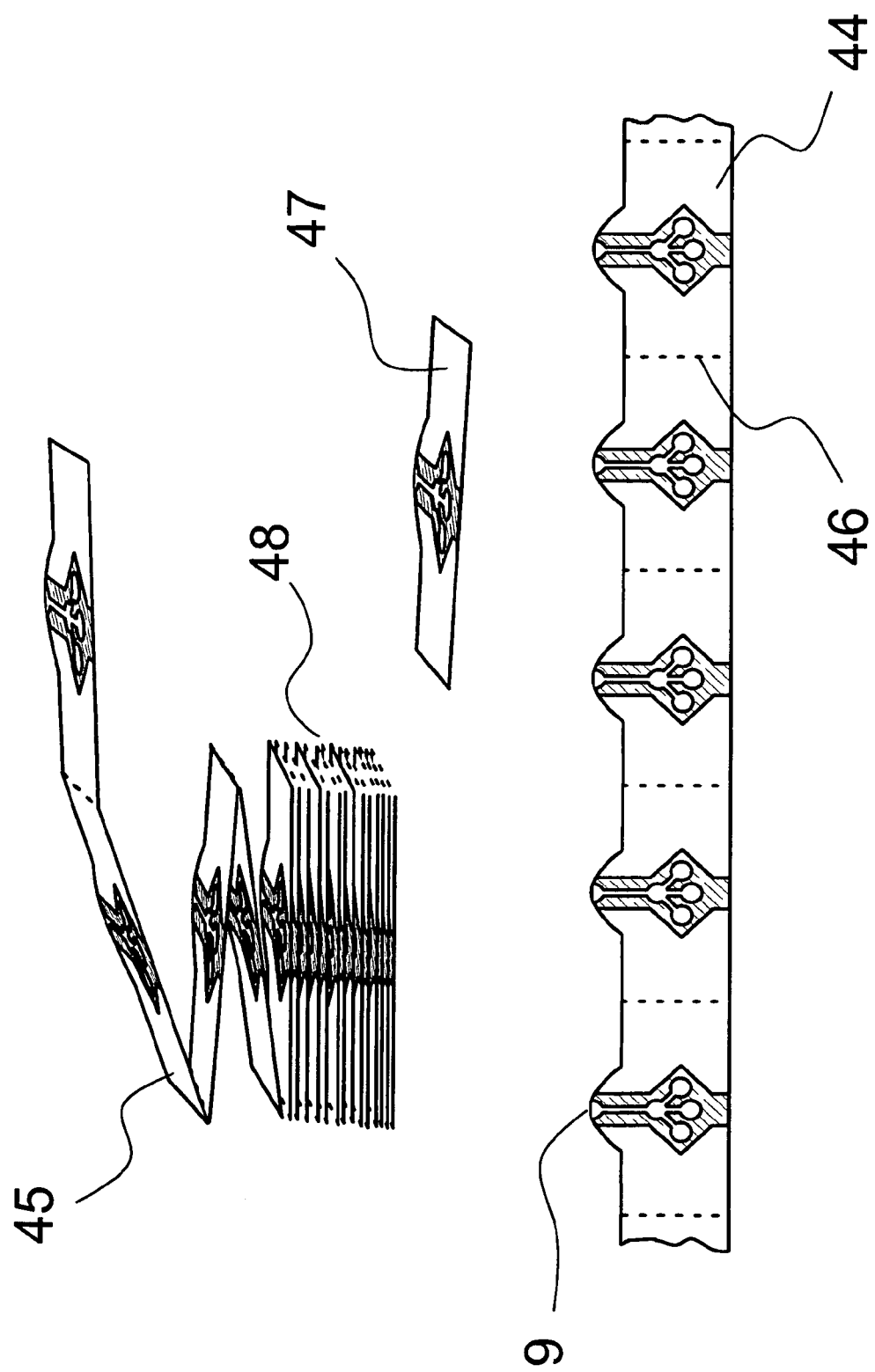
FIG. 18 shows an analyte test bandolier and folded bandolier to build a stack.

FIG. 18 illustrates another possibility to arrange the analyte test elements in a space-saving manner. In this embodiment the analyte test elements are arranged side by side to form a bandolier 44 with a lateral extension to form the sample application areas 9. In the bandolier, the area between two analyte test elements is provided with a perforation or break line 46 to separate a used analyte test element 45 from the unused part of the analyte test bandolier 44. By means of a zigzag-folding along the perforation or break lines 46 it is possible to build an analyte test device bandolier stack 48 which can easily housed in a small container to allow an easier dispensing of the single analyte test elements of the analyte test bandolier.

Preparation Method of the Analyte Test Element

The analyte test element of the present invention, produced in disk or strip form, can easily be prepared by processes to those of ordinary skill in the arts of printing, die punching, and laminating. The design of the analyte test element allows a simple and cost efficient production process, which is preferably but not necessarily of a continuous nature.

In a first step of the preparation method, a pattern of the sample distribution system is formed by creating areas of high and low surface energy on a substrate. In a preferred embodiment, the areas of high surface energy forming the sample pathways and detection areas on the first and second surfaces are created by applying a hydrophilic formulation on a hydrophobic surface of a substrate. As detailed above, it is also possible to create the areas of high and low surface energy by applying a pattern of hydrophobic "guiding elements" on a hydrophilic surface. In case the substrate has an intermediate hydrophobic character, the printing of hydrophilic pathways with surrounding hydrophobic pattern is possible as well.

The substrate may be formed of a material like glass, polyvinyl acetate, poly-methylmethacrylate, poly-dimethyl-siloxane, polyesters and polyester resins containing fluorene rings, polycarbonates and polycarbonate-polystyrene graft copolymers, terminal modified polycarbonates, polyolefins, cycloolefins and cycloolefin copolymers, and/or olefinmaleimide copolymers.

The application of a hydrophilic pattern on a hydrophobic substrate and/or the application of hydrophobic "guiding elements" on a hydrophilic substrate can be accomplished with flexography, lithograph, gravure, solid ink coating methods, or ink-jet-printing processes.

However, the preferred fabrication method is flexography, which allows high-resolution printing on rotary presses and supports high-speed production. It is an established technology for printing on polymer film substrates and widely used in the packaging industry. The optical detection process shown in FIG. 8 requires transparent and clear ink with low viscosity for the hydrophilic pattern. Low viscous inks are preferred to achieve a thin and even coating of about 2-4 microns. The optical window of the ink needs to be in the wave-length range where the indicator dye absorbs the light after the chemical reaction. The requirements for hydrophobic inks, apart from the hydrophobic nature, are less stringed and could be used to decorate the analyte test strip or disk with a desired colour as well. The operation of a four-colour flexography-printing machine is established practice and provides no operational problems. The same holds for lithography device.

Even though solvent based or UV curing inks are applicable to prepare the analyte test element, electron beam (EB) curing inks are much preferred. These inks provide highest resistance to mechanical and chemical factors, and contain 100% polymers, optionally with pigments, but no volatile organic solvents and photo initiators, which have proven to affect the stability of sensor chemistry. These positive gains in performance characteristics are derived from the ability of electrons to form cross-linked polymeric films and to penetrate the surface.

Inks used in EB curing make use of the polymerising capability of acrylic monomers and oligomers. Acrylic chemistry has a special significance in modern day inks. (6 J. T. Kunjappu. "The Emergence of Polyacrylates in Ink Chemistry," Ink World, February, 1999, p. 40.) The structure of the simplest acrylic compound, acrylic acid, is shown in the formula (I)

$$CH_2=CH-COOH \qquad (I)$$

The double bond in the acrylic moiety opens up during interaction with electrons (initiation) and forms a free radical that acts on other monomers forming a chain (propagation) leading to high-molecular-weight polymers. As mentioned before, radiation induced polymerisation requires no external initiator since radiation itself generates free radicals with the result that no initiating species will be left in the coating.

A variety of acrylic monomers are available for EB curing that range from simple acrylates such as 2-phenoxyethyl acrylate and isooctyl acrylate, to pre-polymers like bisphenol A, epoxy acrylate and polyester/polyether acrylates (R. Golden. J. Coatings Technol., 69 (1997), p. 83). This curing technology allows the design of "functional inks" with the focus on the desired chemical and physical properties without the necessity of a solvent and curing systems required by other inks, which may complicate the design process.

Suitable hydrophobic inks will contain monomers, oligomers, and prepolymers with hydrophobic functions like isooctyl acrylates, dodecyl acrylates, styrene derivates or systems with partly fluorinated carbon chains.

Inks with hydrophilic functions can be realised from a wide selection of cross-linkable water-soluble polymers, useful are acrylate derivatives prepared form polyalcohols, polyethylene-glycols, polyethylene-oxides, vinylpyrolidone, alkylphosphocholine derivates and others; particularly useful are organo-modified silicone acrylates, which are a cross-linkable species of organo-modified polysiloxanes. Suitable coatings provide a contact angle with water of typically less than 25° and a surface energy of typically more than 55 mN/m.

The second step of the production process comprises the application of the catalytic formulation, containing an enzyme or another compound undergoing a catalytic or non-catalytic reaction with the analyte and, if necessary a co-enzyme, and an indicator dye, onto the predetermined detection areas of the sample distribution system formed on the substrate providing the first surface, and the application of calibration formulations containing different levels of calibration compound or analyte to the predetermined detection areas of the sample distribution system formed on the substrate providing the second surface.

The accuracy of this deposition step is very critical and defines the precision and performance of the analyte test element. Preferably, both formulations are applied with aid of high precision ink-jet systems or piezoelectric print heads. The catalytic and calibration formulations must be prepared to be highly soluble by the physiological or aqueous fluid sample. Preferably, they are water based. Thus, these inks are mostly composed from water, enzymes, indicators, or calibration compound respectively, and will be dried at slightly elevated temperatures. Main aspect of these ink formulations is the fast reconstitution of chemical components after sample application without compromising the hydrophobic areas of the analyte test element.

The next step comprises the lamination procedure, in which the base and cover layer presenting the first and second surfaces of the sample distribution system are laminated onto a centre layer, thereby defining a distance between the first and second surface of the base and cover layer. The centre layer provides a discontinuity to create a cavity for the sample distribution system in the areas where the sample distribution system is formed on the first and second surface of the base and cover layer. The patterns of high and low surface energy formed on the first and second surface of the base and cover layer must be aligned to be mostly congruent to enable the formation of a functional sample distribution system between the first and second surface.

Precise xy-registration of base and cover layers becomes a critical task for the function of the device, if this registration is not achieved, the sample distribution system will not function properly and/or will have a higher variability with regards to the specified sample volume. Registration tolerances should be within +/−5% of the width of the hydrophilic pathways to achieve good performance.

FIG. 6 shows the top view (left) and cross-section (right) of the analyte test element and the effect of registration quality. In case of 6a the sample distribution system is assembled properly with good alignment of the hydrophilic pathways of the first (2a) and second (4a) surface. The result of an improperly aligned analyte test element is given in FIG. 6b. Although, the spacer between the base (2) and the cover layer (4) is identical in case of 6a and 6b the sample volume is falsely enlarged in case b, since the sample fluid covers partly the hydrophobic guiding elements of the sample distribution system. The effect is caused by the sample fluid inside the analyte test system, which seeks to minimise the surface area exposed to air in order to gain the most favourable energetic state and therefore overriding the effect of the hydrophobic areas.

In an alternative embodiment, as shown in FIG. 6c, the sample distribution system of the cover layer (4) is designed about 10% smaller as the sample distribution system of the base layer (2) thus the total sample volume of the analyte test element is defined by the extensions of the sample distribution system of the base layer, allowing a higher tolerance for the registration process during manufacturing without compromising the precision of the required sample volume. It will be obvious for someone skilled in the art that base and cover layer are exchangeable in the discussed embodiment without affecting the principle of the invention.

The application of the centre layer, which may be a double-sided adhesive tape with a preferred thickness of 80 microns, is less demanding because of the relatively large discontinuity in the material compared to the size of the hydrophilic pathways. Registration is especially important in continuous production lines where the substrate progresses with several meters up to tens of meters per minute. Substrate expansion and web tension make the registration in x-direction (the direction of the web movement) more difficult than the y-direction perpendicular to the web movement.

Figure 19:
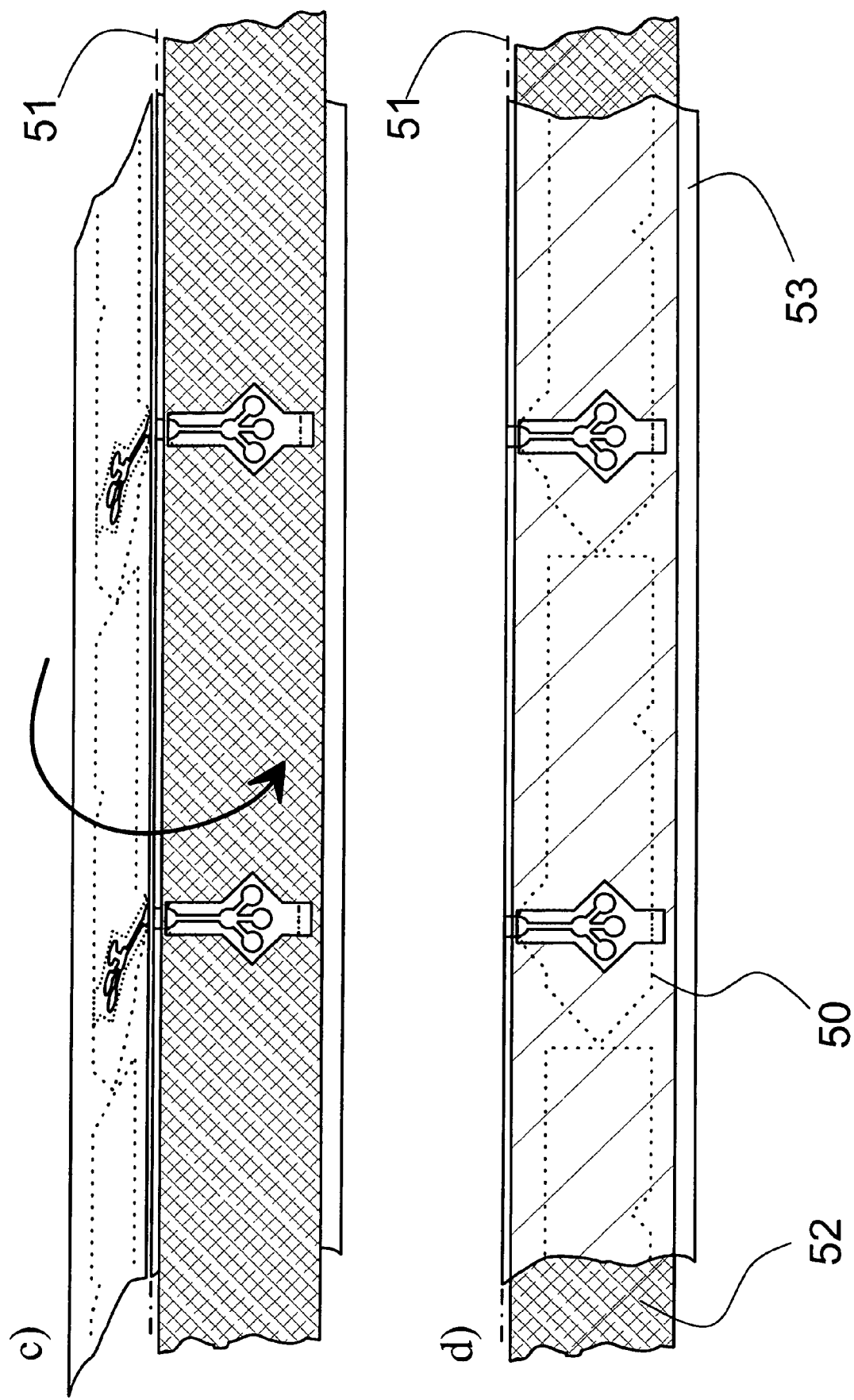
FIG. 19 shows the production steps of the analyte test elements with strip shape.
Figure 19:
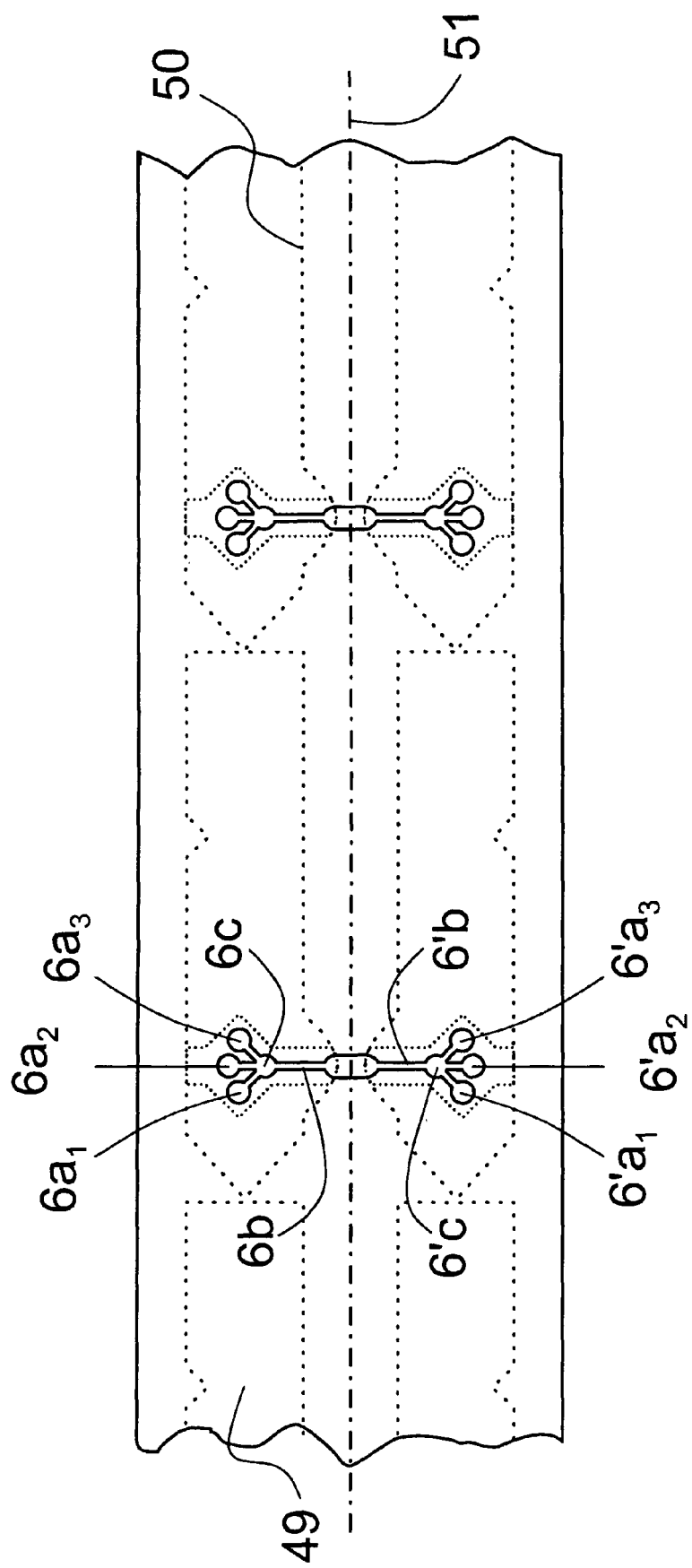
Figure 19:
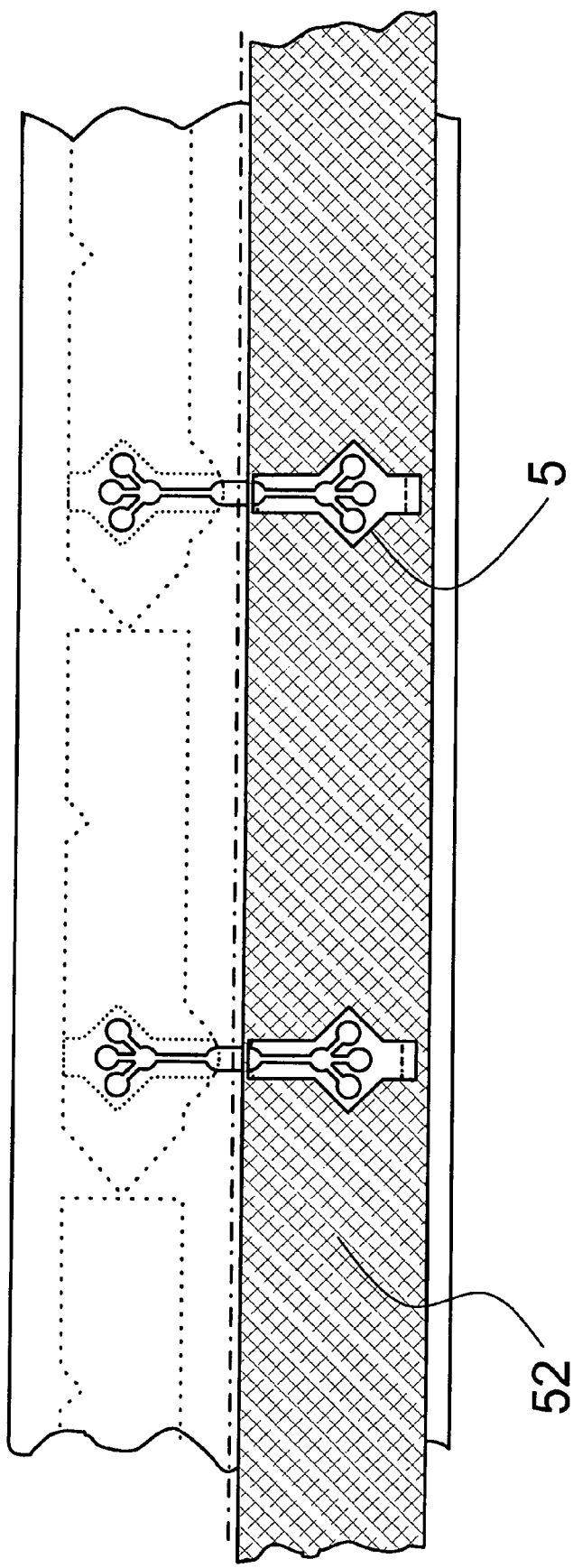

An inventive preparation method for flexible polymer films providing an accurate registration of the patterns of first and second surface is illustrated in FIG. 19 showing parts of a continuous web production process. In a first production step according to FIG. 19a, patterns of the sample distribution system 6 of the base and cover layer are printed on one web substrate 49, which represents the material of the analyte test element and strip, respectively. As illustrated in FIG. 19, the printed patterns of the sample distribution systems 6 are arranged on the web substrates 49 in such a manner that two sample distribution systems are opposite to each other and linked in the areas which form later the sample application areas. Thus, the position of the predetermined detection areas 6a, 6'a is fixed relative to each other and remains unaffected by the material expansion and web tension.

The dotted lines 50 indicate the future cutting lines to segregate the analyte test strips, while the dotted lines 51 indicate the mirror line of the strip artwork and the future fold line of the web substrate.

After printing the sample distribution areas, the detection areas 6a, 6'a of the sample distribution system are coated with the catalytic and calibration formulations. For example, the detection areas 6'a of the lower row of the web substrate 49, which will represent the first surface of the analyte test element, are coated with the catalytic formulation containing the enzyme and an indicator, whereas the detection areas 6a of the upper row of the web substrate 49, which will represent the second surface of the analyte test element, are coated with calibration formulations containing different levels of the calibration compound; one of the calibration formulation (e. g. positioned in $6a_1$) does not contain calibration compound and delivers the reading of the physiological or aqueous fluid in the detection step.

Thereafter, an additionally layer is laminated on one of the surfaces, e. g. the surface 2a of the base layer 2, representing the centre layer 52 of the analyte test element as shown in FIG. 19b. The centre layer 52 may be formed of double-sided adhesive tape, which provides breakthroughs 5 exposing the sample distribution systems 6 and will create a cavity for the sample distribution systems in the analyte test element after the final assembly step.

The analyte test element of the present invention is than assembled by folding the two row sides along the fold line 51, e. g. with help of a folding iron, as illustrated in FIG. 19c creating a folded and laminated web 53 as shown in FIG. 19d. Subsequently, a press roller can secure a tight connection between the centre layer, base and cover layer.

Finally, the laminated web 53 is cut or punched in to the desired product shape, whereas line 50 projects an exemplary shape of the final analyte test strip onto the web 53 before the segregation process. With the preparation method illustrated in FIG. 19 the top part of the substrate can be folded on to the bottom part without the danger of loosing the registration in the x-direction of the web and provides an easier method to get the right registration of the first and second surfaces forming the sample distribution system in comparison to single sheet process.

The present invention provides an analyte test system that incorporates calibration and quality control means in a dry reagent test strip format that does not make excessive demand on the strip production process but eliminates the need for user interventions in calibration and quality control procedures in combination with a tight control of the strip performance at time of sample analysis.

The invention claimed is:

1. An analyte test element for determining the concentration of at least one analyte in a physiological or aqueous sample fluid having a first surface (2a) and a second surface (4a) opposite from each other, said both surfaces are provided with two substantially equivalent patterns forming areas of high and low surface energy which are aligned mostly congruent to create a sample distribution system (6) with at least two detection areas (6a), wherein the applied physiological or aqueous fluid is substantially constrained to the areas with high surface energy, and wherein n predetermined detection areas (6'a) of said first surface (2a) are coated with a catalytic formulation promoting the detection of an analyte in a physiological or aqueous fluid, and n predetermined detection areas (6a) of said second surface (4a) are coated with n calibration formulations made up of m blank formulations and n-m formulations with different levels of calibration compound, whereby n is an integer number larger than 2, m is an integer number equal or larger than 1, and n>m.

2. The analyte test element according to claim 1, wherein the distance between the first and second surface is determined by a centre layer (3) which is arranged between a base layer (2) and a cover layer (4) having the first and second surfaces (2a, 4a).

3. The analyte test element according to claim 2, wherein the centre layer (3) has a discontinuity (5) to form a hollow cavity together with the first and second surface (2a, 4a) of the base and cover layer (2, 4), said hollow cavity being larger than the sample distribution system (6) formed by the areas of high surface energy on the first and second surfaces (2a, 4a).

4. The analyte test element according to claim 1, wherein said areas of high surface energy are created by applying cross-linkable and/or non-soluble hydrophilic and/or amphiphilic agents on the first and second surfaces (2a, 4a).

5. The analyte test element according to claim 4, wherein said hydrophilic agents are selected from the group consisting of functionalised derivates from polyalcohols, polyethylene-glycols, polyethylene-oxides, vinylpyrrolidones and organo-modified polysiloxanes or alkyl-phosphocholine polyethylene-glycol copolymers.

6. The analyte test element according to claim 1, wherein said first surface (2a) and second surface (4a) are hydrophobic and non-wettable by a physiological or aqueous fluid and transparent for light particular in the UV, near IR and/or visible range of the electromagnetic spectrum.

7. The analyte test element according to claim 1, wherein said areas of low surface energy are created by applying a hydrophobic composition on the first and second surfaces (2a, 4a), said hydrophobic composition preventing the wetting of the coated area by a physiological or aqueous fluid.

8. The analyte test element according to claim 7, wherein said hydrophobic composition contains isooctyl acrylates, dodecyl acrylates, styrene derivates, or systems with partly fluorinated carbon chains.

9. The analyte test element according to claim 1, wherein said first surface (2a) and second surfaces (4a) are hydrophilic and wettable for the physiological or aqueous fluid and transparent for light particular in the UV, near IR and/or visible range of the electromagnetic spectrum.

10. The analyte test element according to claim 9, wherein said first surface (2a) and second surface (4a) are rendered hydrophilic by physical or chemical vapour deposition of hydrophilic compounds.

11. The analyte test element according to claim 1, wherein the base layer (2) and cover layer (4) providing the first and second surfaces (2a, 4a) are formed of a material selected from the group consisting of glass, polyvinyl acetate, polymethyl-methacrylate, polydimethyl-siloxane, polyesters and polyester resins containing fluorene rings, polycarbonates and polycarbonate-polystyrene graft copolymers, terminal modified polycarbonates, polyolefins, cycloolefins and cycloolefin copolymers, and/or olefin-maleimide copolymers.

12. The analyte test element according to claim 1, wherein an additionally detection area (6c) is provided which neither contains the catalytic compound nor the calibration compound, enabling the measurement of background signals.

13. The analyte test element according to claim 1, wherein said catalytic formulation coated on n predetermined detection areas (6'a) of first surface (2a) allows the detection of an analyte concentration contained in a physiological or aqueous fluid sample using transmission or absorbance photometry.

14. The analyte test element according to claim 1, wherein said calibration compound contained in the calibration formulation coated on n-m predetermined detection areas (6a) of second surface (4a) is identical or substantially equivalent to the analyte and able to induce the same chemical reaction in the catalytic formulation as the analyte in the physiological or aqueous fluid sample.

15. The analyte test element according to claim 14, wherein the calibration compound is glucose.

16. The analyte test element according to claim 1, wherein the catalytic formulation contains as reactive components a promoter undergoing a catalytic or non-catalytic reaction with the analyte, and/or a co-enzyme, and an indicator generating an optically detectable product.

17. The analyte test element according to claim 16, wherein the promoter is an enzyme selected from the group consisting of dehydrogenases, kinases, oxidases, phosphatases, reductases and/or transferases.

18. The analyte test element according to claim 17, wherein the promoter is an enzyme specific for glucose.

19. The analyte test element according to claim 16, wherein the indicator to determine the analyte concentration is selected from the group consisting of aromatic amines, aromatic alcohols, azines, benzidines, hydrazones, aminoantipyrines, conjugated amines, conjugated alcohols, and/or aromatic and aliphatic aldehydes.

20. The analyte test element according to claim 1, wherein the calibration formulation applied to the predetermined detection areas (6a) of second surface (4a) contains an inert water-soluble dye in a predetermined and fixed ratio to the calibration compound allowing a suitable reading device to evaluate the concentration of the calibration compound within the calibration formulation with a wave length different from the wave length used to measure the reaction product of the catalytic formulation with the analyte.

21. The analyte test element according to claim 20, wherein said inert water-soluble dye is selected from the group consisting of brilliant black BN; brilliant blue G; carmoisine; coumarin 120; direct blue 2B; indigo carmine; new coccine; ponceau 4R; rhodamine 19; sunset yellow; tartrazine; and/or a water soluble derivate of malachite green.

22. The analyte test element according to claim 1, wherein a sample application area (9) is located at the end of a convex and lateral extension (10) on one side of said analyte test element.

23. An analyte test arrangement including a plurality of devices according to claim 1, which are arranged symmetrically around a centre point to form an analyte test disk (31) with outward facing sample application areas (39).

24. An analyte test arrangement including a plurality of devices according to claim 1, which are arranged in a linear manner to form an analyte test bandolier (44) with lateral extensions forming the sample application areas (9).

25. An analyte test element for determining the concentration of at least one analyte in a physiological or aqueous sample fluid having a first surface and a second surface opposite from each other, wherein one of the first and second surface is provided with a hydrophilic/hydrophobic pattern and the corresponding surface provides a homogeneous pattern of hydrophilic pixels surrounded by a hydrophobic area therefore creating overall a surface with semi hydrophilic and semi hydrophobic character, whereby the hydrophilic and semi hydrophilic areas create a sample distribution system with at least two detection areas and wherein n predetermined detection areas (6'*a*) of said first surface (2*a*) are coated with a catalytic formulation promoting the detection of an analyte in a physiological or aqueous fluid, and n predetermined detection areas (6*a*) of said second surface (4*a*) are coated with n calibration formulations made up of m blank formulations and n-m formulations with different levels of calibration compound, whereby n is an integer number larger than 2, m is an integer number equal or larger than 1, and n>m.

* * * * *